US009131904B2

(12) United States Patent
Qualey et al.

(10) Patent No.: US 9,131,904 B2
(45) Date of Patent: Sep. 15, 2015

(54) CONFIGURABLE PATIENT MONITORING SYSTEM

(75) Inventors: Bruce Dean Qualey, Mill Creek, WA (US); Scott Richard Britt, Duvall, WA (US); Gary Ninneman, Sammamish, WA (US); Roy Hays, Seattle, WA (US)

(73) Assignee: Spacelabs Healthcare LLC, Snoqualmie, WA (US)

( * ) Notice: Subject to any disclaimer, the term of this patent is extended or adjusted under 35 U.S.C. 154(b) by 620 days.

(21) Appl. No.: 13/300,462

(22) Filed: Nov. 18, 2011

(65) Prior Publication Data

US 2012/0127103 A1 May 24, 2012

Related U.S. Application Data

(60) Provisional application No. 61/415,799, filed on Nov. 19, 2010, provisional application No. 61/486,307, filed on May 15, 2011.

(51) Int. Cl.
| | |
|---|---|
| G06F 15/16 | (2006.01) |
| G06F 3/045 | (2006.01) |
| G06F 3/044 | (2006.01) |
| A61B 5/15 | (2006.01) |
| H05K 7/00 | (2006.01) |
| A61B 5/00 | (2006.01) |
| A61B 5/0205 | (2006.01) |

(52) U.S. Cl.
CPC .............. *A61B 5/7445* (2013.01); *A61B 5/002* (2013.01); *A61B 5/742* (2013.01); *A61B 5/02055* (2013.01); *A61B 5/746* (2013.01)

(58) Field of Classification Search
USPC ................ 345/173; 368/10; 600/300, 301
See application file for complete search history.

(56) References Cited

U.S. PATENT DOCUMENTS

| | | | | |
|---|---|---|---|---|
| 5,087,906 | A | * | 2/1992 | Eaton et al. .................. 340/7.61 |
| 5,262,944 | A | | 11/1993 | Weisner |
| 5,348,008 | A | | 9/1994 | Bornn |

(Continued)

FOREIGN PATENT DOCUMENTS

| | | |
|---|---|---|
| WO | 9415523 | 7/1994 |
| WO | 9918705 | 4/1999 |
| WO | 2010126916 | 11/2010 |

OTHER PUBLICATIONS

International Search Report for PCT/US2011/61557, Apr. 23, 2012.

(Continued)

*Primary Examiner* — Grant Sitta
(74) *Attorney, Agent, or Firm* — Novel IP

(57) ABSTRACT

A system for patient monitoring includes a plurality of non-integrated components including a display, a monitor, one or more modules, and at least one patient parameter measuring device. The display includes a flat glass front with a blackened border that appears continuous but allows the passage of light during alarm situations. The display includes a housing with openings on the right and left sides which allow the passage of light during alarm situations. The display also includes a prominent programmable button which enables easy alarm silencing. The monitor can be fixedly attached to the back of the display in a "backpack mounting" configuration to free up bedside space. Optional monitor and display cabinets are capable of housing power supplies and cables and provide for additional free space. The monitor, module (s), and patient parameter measuring device(s) are all interconnected via Dual Serial Bus (DSB) interfaces.

20 Claims, 27 Drawing Sheets

(56) References Cited

U.S. PATENT DOCUMENTS

| | | | |
|---|---|---|---|
| 5,586,909 A | 12/1996 | Saba | |
| 5,787,298 A | 7/1998 | Broedner | |
| 5,819,741 A * | 10/1998 | Karlsson et al. | 600/523 |
| 6,050,940 A | 4/2000 | Braun | |
| 6,435,690 B1 * | 8/2002 | Till | 362/88 |
| 6,600,662 B1 * | 7/2003 | Emmert et al. | 361/814 |
| 6,674,837 B1 | 1/2004 | Taskar | |
| 6,735,648 B2 | 5/2004 | Onishi | |
| 7,024,569 B1 | 4/2006 | Wright | |
| RE39,233 E | 8/2006 | McGrath | |
| 7,223,007 B1 * | 5/2007 | Fredley et al. | 362/616 |
| 7,336,980 B1 * | 2/2008 | Kaikuranta et al. | 455/575.6 |
| 7,751,878 B1 | 7/2010 | Merkle | |
| 2001/0018332 A1 * | 8/2001 | Lustila et al. | 455/90 |
| 2002/0108011 A1 | 8/2002 | Tanha | |
| 2003/0130590 A1 | 7/2003 | Bui | |
| 2003/0171898 A1 | 9/2003 | Tarassenko | |
| 2003/0210780 A1 * | 11/2003 | Pratt et al. | 379/428.01 |
| 2004/0021705 A1 * | 2/2004 | Baker et al. | 347/2 |
| 2004/0054261 A1 | 3/2004 | Kamataki | |
| 2004/0117209 A1 | 6/2004 | Brown | |
| 2004/0147818 A1 | 7/2004 | Levy | |
| 2004/0221077 A1 | 11/2004 | Yen | |
| 2005/0033124 A1 | 2/2005 | Kelly | |
| 2005/0059924 A1 | 3/2005 | Katz | |
| 2005/0065417 A1 | 3/2005 | Ali | |
| 2005/0146431 A1 | 7/2005 | Hastings | |
| 2005/0151640 A1 | 7/2005 | Hastings | |
| 2006/0199618 A1 * | 9/2006 | Steer et al. | 455/567 |
| 2006/0258926 A1 | 11/2006 | Ali | |
| 2007/0032749 A1 | 2/2007 | Overall | |
| 2007/0060869 A1 | 3/2007 | Tolle | |
| 2007/0180140 A1 | 8/2007 | Welch | |
| 2007/0255116 A1 | 11/2007 | Mehta | |
| 2008/0039701 A1 | 2/2008 | Ali | |
| 2008/0170287 A1 * | 7/2008 | Champion et al. | 359/275 |
| 2008/0177160 A1 | 7/2008 | Al Ali | |
| 2008/0177397 A1 | 7/2008 | Davlin | |
| 2008/0281168 A1 | 11/2008 | Gibson | |
| 2009/0005703 A1 | 1/2009 | Fasciano | |
| 2009/0069642 A1 | 3/2009 | Gao | |
| 2009/0117784 A1 | 5/2009 | Wu | |
| 2009/0124239 A1 * | 5/2009 | Tsuei | 455/414.1 |
| 2009/0149901 A1 | 6/2009 | Jayne | |
| 2009/0182204 A1 | 7/2009 | Semler | |
| 2009/0192541 A1 | 7/2009 | Ortiz | |
| 2009/0193315 A1 | 7/2009 | Gower | |
| 2010/0004539 A1 * | 1/2010 | Chen et al. | 600/445 |
| 2010/0164452 A1 | 7/2010 | Ruan | |
| 2010/0179400 A1 * | 7/2010 | Brauker et al. | 600/309 |
| 2010/0233891 A1 | 9/2010 | Broeksteeg | |
| 2010/0238138 A1 | 9/2010 | Goertz | |
| 2010/0261979 A1 | 10/2010 | Kiani | |
| 2010/0294405 A1 * | 11/2010 | Longinotti-Buitoni | 150/165 |
| 2010/0298718 A1 * | 11/2010 | Gilham et al. | 600/484 |
| 2010/0324380 A1 | 12/2010 | Perkins | |
| 2011/0130798 A1 * | 6/2011 | Elghazzawi et al. | 607/5 |
| 2011/0152629 A1 | 6/2011 | Eaton | |
| 2011/0164074 A1 * | 7/2011 | Frank et al. | 345/690 |
| 2011/0257489 A1 | 10/2011 | Banet | |
| 2011/0279383 A1 * | 11/2011 | Wilson et al. | 345/173 |
| 2012/0030610 A1 * | 2/2012 | Diperna et al. | 715/773 |
| 2012/0075327 A1 * | 3/2012 | Mackenzie | 345/589 |
| 2012/0127103 A1 * | 5/2012 | Qualey et al. | 345/173 |

OTHER PUBLICATIONS

International Search Report for PCT/US2011/061554, Feb. 14, 2014.
International Search Report for PCT/US2011/061555, Apr. 17, 2012.
International Search Report for PCT/US2011/061558, Aug. 10, 2012.
International Preliminary Report on Patentability for PCT/US2011/061554, Feb. 25, 2014.

* cited by examiner

CONFIGURABLE PATIENT MONITORING SYSTEM

CROSS-REFERENCE TO RELATED APPLICATIONS

The present specification claims priority from U.S. Provisional Patent Application No. 61/415,799, entitled "Patient Monitoring System with Dual Serial Bus (DSB) Interface" and filed on Nov. 19, 2010, which is herein incorporated by reference in its entirety.

In addition, the present specification claims priority from U.S. Provisional Patent Application No. 61/486,307, entitled "User Configurable Central Monitoring Station", filed on May 15, 2011 and herein incorporated by reference in its entirety.

Co-pending U.S. patent application Ser. No. (to be determined), entitled "Self-Contained Patient Monitor", filed on Nov. 18, 2011 and assigned to the applicant of the present invention, is also herein incorporated by reference in its entirety.

Co-pending U.S. patent application Ser. No. (to be determined), entitled "Dual Serial Bus Interface", filed on Nov. 18, 2011 and assigned to the applicant of the present invention, is also herein incorporated by reference in its entirety.

FIELD

The present specification relates generally to hospital-based patient monitoring systems. More particularly, the present specification relates to a configurable patient monitoring system comprised of an external display, a monitor, one or more modules, and a plurality of devices to measure patient parameters.

BACKGROUND

A patient monitoring system is an electronic medical device that measures a patient's various vital signs, collects and processes all measurements as data, and then displays the data graphically and/or numerically on a viewing screen. Graphical data is displayed continuously as data channels on a time axis (waveforms). Patient monitoring systems are positioned near hospital beds, typically in critical care units, where they continually monitor patient status via measuring devices attached to the patient and can be viewed by hospital personnel. Some patient monitoring systems can only be viewed on a local display, whereas others can be joined to a network and thereby display data at other locations, such as central monitoring or nurses' stations.

Portable patient monitoring systems are available for use by emergency medical services (EMS) personnel. These systems typically include a defibrillator along with the monitor. Other portable units, such as Holter monitors, are worn by patients for a particular time period and then returned to the physician for evaluation of the measured and collected data. Current patient monitoring systems are able to measure and display a variety of vital signs, including, pulse oximetry ($SpO_2$), electrocardiograph (ECG), invasive blood pressure (IBP), non-invasive blood pressure (NIBP), electroencephalograph (EEG), body temperature, cardiac output, capnography ($CO_2$), mixed venous oxygen saturation ($SvO_2$), bispectral index (BISx), and respiration. Patient monitoring systems are capable of measuring and displaying maximum, minimum, and average values and frequencies, such as pulse and respiratory rates.

Data collected can be transmitted through fixed wire connections or wireless data communication. Power to patient monitoring systems can be supplied through a main power line or by batteries. While current patient monitoring systems are effective in monitoring patient conditions and notifying medical personnel of changes, they are not without certain drawbacks and limitations.

Patient monitoring systems are typically equipped with audio and visual alarms to notify medical personnel of changes in the patient's status. The alarm parameters can be set by the medical personnel. Audible nurse alarms can often be too loud and distracting to other patients and personnel. Bright, flashing visual nurse alarms can also be distracting to other patients. Conversely, more subtle visual nurse alarms can be too difficult to visualize, which can be a result of visual clutter on the monitoring system display or because the visual alarm is not differentiated enough from other information on the display. In addition, it can be difficult for nurses to silence an active alarm, delaying care to the patient. The typical user interface for alarm control is operated via traditional pushbuttons or in many instances a touchscreen or keyboard.

Therefore, a need exists for a better alarm mechanism within patient monitoring systems, in which both the audible and visual alarms are easily recognized by the nurses while not disturbing patients. In addition, there is a need for an alarm mechanism in which an attending nurse can quickly silence the alarm and then focus on the patient's needs.

Current patient monitoring systems are traditionally bundled into an integrated package that includes the display, enclosure, and electronics. This limits flexibility and prevents users from customizing the monitoring system to their specific needs and available space. Therefore, a need exists for a modular patient monitoring system in which the individual components are discrete and can be connected in various configurations. Specifically, a need exists for a monitor that does not have an integrated display and can connect to a custom or commercial, off-the-shelf (COTS) display. Such a monitoring system would enable users to position the display and monitor in the most efficient manner, thereby freeing up valuable area in the patient vicinity.

SUMMARY

The present specification is directed toward a configurable patient monitoring system comprised of a plurality of non-integrated components including a display, a monitor, one or more modules, and at least one patient parameter measuring device. A variety of patient parameters can be monitored and the parameter measuring devices are connected to the system via Dual Serial Bus (DSB) connectors and DSB cables.

In one embodiment, the present specification is directed toward a display device for use in patient monitoring systems, comprising: a housing having a front face and defining an enclosure, wherein said enclosure comprises a first opening on a right side of said housing and a second opening on a left side of said housing; a touchscreen mounted to the front of said housing, wherein said touchscreen comprises a flat piece of glass having a central display area and a black border that extends along a left, right, top, and bottom edge of said glass; a processor for determining an alarm state; and, light sources within said touchscreen which are activated by said processor during the alarm state, wherein said light sources are configured to pass through said black border and concurrently pass through said first opening and second opening.

In one embodiment, the display device further comprises a single prominent, programmable capacitive button along the border of said touchscreen. In one embodiment, the button comprises a metal capacitive piece. In another embodiment, the display device includes a section of the touchscreen programmed for control of the alarm light.

In one embodiment, the black border of the display device is silk-screened on the back of the glass. In another embodiment, the black border of the display device is comprised of an ink that is silk-screened or sprayed onto a masked out border area on the back of the glass. In another embodiment, the black border of the display device contains small apertures that make the border appear continuous and uniform but allow light to pass through.

In one embodiment, the light sources which emit light passing through the black border are the same light sources which emit light passing through the first opening and second opening.

In one embodiment, the light sources which emit light passing through the black border are different than the light sources which emit light passing through the first opening and second opening.

In another embodiment, the present specification is directed towards a system for patient monitoring comprising: at least one patient monitor that allows for communication with external devices, wherein said patient monitor is in electronic communication with and drives at least one display, and wherein said display comprises: a housing having a front and defining an enclosure, wherein said enclosure comprises a first opening on a right side of said housing and a second opening on a left side of said housing; a touchscreen mounted to the front of said housing, wherein said touchscreen comprises a flat piece of glass having a central display area and a black border that extends along a left, right, top, and bottom edge of said glass; at least one module for providing measurements of a plurality of patient parameters, wherein said module is in electronic communication with said patient monitor and wherein said module comprises at least one interface for electronically communicating with at least one patient parameter measurement device; a processor for determining an alarm state; and, light sources within said touchscreen which are activated by said processor during the alarm state, wherein said light sources are configured to pass through said black border and concurrently pass through said first opening and second opening; and at least one Dual Serial Bus (DSB) interface for enabling electronic communication between the patient monitor, module, and/or patient parameter measuring device.

In one embodiment, the patient monitor is docked on the rear surface of the display in a "backpack mounting" configuration.

In one embodiment, the system for patient monitoring further comprises a display mounting cabinet.

In one embodiment, the system for patient monitoring further comprises a monitor mounting cabinet.

In one embodiment, the system for patient monitoring further comprises a handle attached to the at least one display.

BRIEF DESCRIPTION OF THE DRAWINGS

These and other objects and advantages of the present specification will become more fully apparent from the following detailed description when read in conjunction with the accompanying drawings with like reference numerals indicating corresponding parts through-out, wherein.

DETAILED DESCRIPTION

Figure 1:
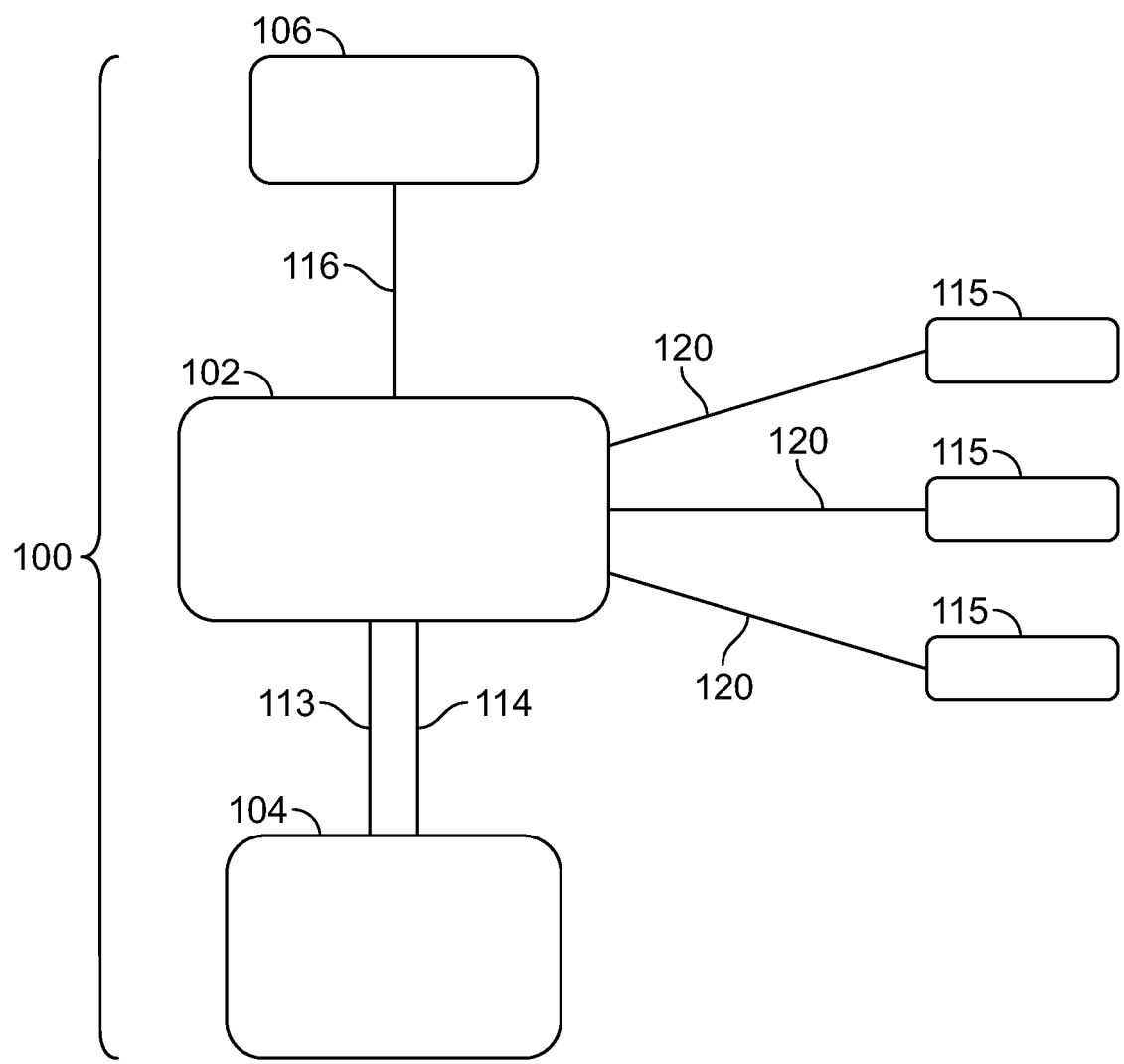
FIG. 1 is a block diagram depicting one embodiment of an exemplary configuration of the components of the patient monitoring system of the present specification, illustrating the use of Dual Serial Bus (DSB) cables to connect patient parameter measuring devices to the monitor.

In one embodiment, the present specification is directed toward a configurable patient monitoring system comprised of a plurality of non-integrated components including a display, a monitor, one or more modules, and at least one patient parameter measuring device. A variety of patient parameters can be monitored and the parameter measuring devices are connected to the system via Dual Serial Bus (DSB) connectors and DSB cables.

The DSB interface comprises a first serial protocol and a second serial protocol, wherein the first protocol is a Universal Serial Bus (USB), Firewire, or Ethernet protocol and the second serial protocol is a Low Power Serial (LPS) protocol. The DSB interface manages power distribution within the system by providing 5 V via the USB protocol or 3.3 V via the LPS protocol to connected devices. Within the DSB interface, each component of the patient monitoring system is a DSB Host, DSB Device, or, both a DSB Host and DSB Device. A DSB Host is in communication with and can supply operating and battery charging power to a connected DSB Device and additionally contains a switched Auxiliary Voltage Supply (AVS) which can provide up to 15 W of power to attached DSB Devices for battery charging or other high power needs. The DSB host recognizes the power requirements of the attached devices and switches power delivery accordingly. The DSB interface is presented in greater detail in co-pending U.S. patent application Ser. No. (TBD), entitled "Dual Serial Bus Interface", filed on Nov. 18, 2011 and assigned to the Applicant of the present invention, which is hereby incorporated by reference.

External Display and Alarm Indicators

In one embodiment, the patient monitoring system includes an external display that is connected to and driven by the patient monitor. In one embodiment, the external display is capable of depicting up to eight waveforms. In one embodiment, the external display contains speakers that can be connected to the patient monitor's audio output to optionally drive audio alarms at the display.

In one embodiment, the external display contains integrated visual alarm lights located on the front and sides of the display. These alarm lights are larger than current visual alarms, providing a better visual indicator to medical personnel during alarm situations. In one embodiment, the alarm lights flash red, yellow, and cyan to indicate high, medium, and low priority alarms respectively. A continuous, flat piece of glass occupies the entire front of the display and sets into a metal band that wraps the exterior sides of the display for robustness. The piece of glass contains no bezels and doubles as both a touchscreen and as the lens and means of light dispersion for the visual alarm, resulting in a reduced part count. The flat touchscreen glass also provides a continuous surface presented at the front. This makes cleaning easier as there are no edges as found in typical bezel implementations which provide crevices for accumulation of contaminants.

A light source behind the glass transmits appropriate wavelengths of light to indicate alarms. In one embodiment, a black border is silk-screened on the back of the glass around the perimeter. In one embodiment, the black border is comprised of an ink that is silk-screened or sprayed onto a masked out border area that gives the appearance of a continuous and uniform black border but allows light to pass through when the alarm is activated, yielding a visual alarm.

In another embodiment, the border area that is used for the visual alarm contains small apertures that make the border appear continuous and uniform but allow light to pass through. This provides a clean, flat modern appearance that shows no indication of alarm until an actual alarm occurs.

In one embodiment, openings that permit light to flow through for the side alarms are insert-molded into the rear enclosure, allowing for alarm visualization from a full 360 degrees around the display.

In one embodiment, the light source for the side alarms is the same as for the front facing alarms. In another embodiment, the side alarms receive their illumination from a different light source.

In one embodiment, the nurse alarm signals, including flash rates for the display and audio for the audible alarms, are driven and controlled by the monitor through a single cable. In one embodiment, the cable is a RJ50 10-pin locking connector that prevents accidental disconnect when mated to a 10-conductor 26AW Ground Cable. This allows the alarm signals to be exported to other external displays and alarm systems.

In one embodiment, the external display contains an ambient light sensor that senses the brightness level of the environment and adjusts the display brightness accordingly. In a darker or poorly lit environment, the ambient light sensor will automatically dim the display and the alarm lights. This is particularly beneficial for instances in which the patient is sleeping, as dimmer lights will be less likely to disturb the patient. In a brighter or well-lit environment, the ambient light sensor will automatically brighten the display. This feature can be deactivated by a button on the display.

In one embodiment, the external display contains integrated cable hooks to route and position cables. The cable hooks are composed of an injection molded, flexible material that will not mar cables and can flex to hold larger bundles of cables. The cable hooks snap into the lower back of the display and can be mounted either horizontally or vertically. In one embodiment, the snap-in hook is designed to detach from the display if excessive force is applied to the cable, such as, but not limited to, a patient getting out of bed. This allows for the hooks to disengage without damaging the display.

In one embodiment, the external display contains a capacitive button on the front of the touchscreen that can be programmed by the user to perform a variety of functions. In various embodiments, the button is a metal plate or other conductive material utilizing any commonly used touch and/or pressure sensitive technologies. The button is large and positioned prominently as compared to a smaller touch screen button so that it can be accessed easily. In one embodiment, the button is located on the top edge of the front of the display. In another embodiment, the button is located on the bottom edge of the display. In another embodiment, the button is located on the left edge of the display. In another embodiment, the button is located on the right edge of the display. In addition, the button is easier to find because it is not obscured by the clutter of other buttons or user interface items. Circuitry in the monitor senses when the button is touched by an operator and the monitor executes the programmed function.

In one embodiment, the button is programmed to suspend alarm when touched. This allows medical personnel to quickly silence an alarm and reset the alarm indications, so that they can tend to the patient's needs and prevent disturbance to other patients in the area. Since alarms are produced in response to critical events, it is important that the means for silencing and/or resetting them be easy to find and quick to activate. In another embodiment, the button is programmed to admit patient when touched. In another embodiment, the button is programmed to initiate NIBP measurement when touched. In another embodiment, the button is programmed to return the display to its home screen when touched. In yet another embodiment, the button is programmed to print the display when touched. The button would primarily be programmed to suspend alarm to simplify the action required by a nurse to silence an alarm. However, one skilled in the art will understand that the button could be programmed to perform a variety of functions not limited to those listed above.

In another embodiment, the external display contains includes a section of the touchscreen programmed for control of the alarm light.

In another embodiment, the external display contains an optional handle that is mounted to the back of the display and extends out of the bottom of the display. The handle enables one-handed manipulation of the position of the display while a medical professional attends to a patient.

In one embodiment, the external display contains a back-lit power button on the side with a power symbol that is amber when the display is not receiving a video signal and green when a video signal is present. The power button is also encircled by an illuminated ring.

The external display additionally contains a Digital Visual Interface (DVI) port to connect with the monitor of the patient monitoring system and a Video Graphics Array (VGA) port to connect with other monitors. The display is housed with a metal band and a powder coated finish. The back of the display contains two mounting patterns for standard 100 mm Video Electronics Standards Association (VESA) and 75 mm VESA mounts.

Monitor

In one embodiment, the patient monitoring system also includes a monitor that interfaces with the modules and allows for communication with external devices. The monitor is similar to a CPU tower and provides a dock for parameter modules and recorders. In one embodiment, the monitor contains two bays that provide power and communication for up to two proprietary Spacelabs modules. In one embodiment, the monitor can support both current and old modules and also front end device (FED) patient parameter cables. In one embodiment, the monitor contains four USB ports to interface with devices including, but not limited to, keyboards, mice, bar code scanners, and thumb drives. In one embodiment, the front panel of the monitor contains five Dual Serial Bus (DSB) ports to allow for connection to front end device (FED) patient parameter cables. A Patient Worn Hub (PWH), a small, portable self-contained monitor described in co-pending U.S. patent application Ser. No. (TBD) entitled "Self-Contained Patient Monitor", filed on Nov. 18, 2011 and assigned to the Applicant of the present invention, which is hereby incorporated by reference, can also be connected at a DSB port. The PWH can also communicate wirelessly with the monitor. In these scenarios, the monitor acts as the DSB Host and the PWH is the DSB Device.

In addition, third party devices can be connected to the monitor via Device Interface Cables, which translate the output of the third party device to the protocol embedded within the DSB connector. The Device Interface Cable has a DSB connector at one end and a cable connector at the other end to interface with the host and the third party device respectively. The Device Interface Cable is described in greater detail along with the PWH in the application referenced directly above.

The monitor also contains an external audio jack to allow for activation of an external speaker for alarm tones, respiration tones, and any other desired tones. In addition, the monitor contains an internal speaker for alarm tones and any other desired tones. In one embodiment, the monitor contains two DVI ports to allow for connection to two independent external displays. The monitor also contains an Ethernet port for communication with other monitors and hospital infrastructures.

In one embodiment, the monitor contains a port for an external nurse alarm. This port is used for communication with an external display as described above. In one embodiment, one port is employed to carry both the signal to activate the alarm lights and the alarm audio, eliminating the need for two discrete cables and two discrete ports. In one embodiment, the monitor contains an additional nurse alert port that can be used with a stand-alone (not in a display) external nurse alert. The monitor also contains a Synchronous Data Link Control (SDLC) port for communication with expansion module bays that allows users to use more modules through one device. In one embodiment, the monitor contains two serial ports for touch screen communication, software updates and data logging. In one embodiment, the monitor contains a high level output connector on the back that allows the user to sync up defibrillators with ECG output. In one embodiment, power is supplied to the monitor via an external power supply. The monitor also contains a rechargeable battery that is used in the event of power interruption for back-up of module data, powering external nurse alerts, and powering the infrared (IR) receiver.

In one embodiment, the monitor utilizes Dynamic Network Access (DNA) to bring lab, pharmacy, charting, intranet, and Hospital Information System (HIS) applications to the bedside. Medical personnel are able to access this information using a Citrix thin client application running on the monitor. This requires a Citrix server to host the application to serve to the monitors. Nurses and physicians can review information from multiple sources without leaving the patient care area. Concise and complete electronic patient records are created effortlessly. In one embodiment, the monitor includes data shuffle and bar code scanner support for fast, error-free identification and transfer of patient information. With the DNA option, instant access to patient information is assured across the network. This results in assuring optimum patient safety while simultaneously maximizing caregiver efficiency. In one embodiment, the special feature Full Bed Review gives the nurse or physician the ability to remotely view, control, review, and record patient data for any other networked or telemetry bed without leaving the patient's bedside. In one embodiment, the special feature Remote View/Alarm Watch allows the caregiver to see any parameter for any monitored patient on the network from any bedside. During an alarm state, waveforms and numerical data may be saved and recorded for later review. In one embodiment, the special feature Alarm Limit Review provides the caregiver a snapshot view of bedside alarm limits for all active parameters for viewing or printing. In one embodiment, the special feature ICS Clinical Event Interface instantaneously transmits alarms and waveforms to personal communication devices for immediate viewing, resulting in quicker response times. In one embodiment, flexport interfaces link patient data from standalone devices, consolidating waveforms, data, and alarms within the monitor. Information is then integrated directly into the monitor trends for output to HIS and CIS applications.

In one embodiment, the monitor includes a cable cover with an optional printer. The cable cover snaps into the monitor to cover all cable connections to the back of the monitor. The cable cover can be mounted with the opening facing the top or the bottom of the monitor so that the cables can be routed in either direction. The cable cover is fastened to the monitor with a tether so that said cable cover cannot be lost from the unit. In one embodiment, the cable cover can integrate a thermal printer to expand the capabilities of the monitor. In one embodiment, the printer accepts 50 mm paper. In one embodiment, the side enclosures of the monitor are pinned together using a long screw passing through the two enclosure halves. The two halves are fastened to the front bezel and held together by the screw. In one embodiment, the monitor includes optional feet to mount it to a tabletop. In one embodiment, the monitor includes a cover for the DSB connectors when they are not in use. In one embodiment, the monitor contains a back-lit power button on the front of the monitor in which the center power symbol and an encircling ring turn green when the power is on.

"Backpack Mounting" and Cabinets

In one embodiment, the monitor includes a bracket that allows the monitor to be mounted behind the external display. In this configuration, the mounting is termed "backpack mounting" and the cables for measuring the patient parameters extend from the side of the monitor. The mounting of the monitor is reversible so that the cables can extend from either the right side or the left side of the monitor. This allows for cable management to be better situated based on bed and monitor location. The external display is contoured to "nest" the monitor and bracket to give the appearance of one unit. As the display is the primary place of interaction, placing the monitor behind the display gives the overall system a cleaner appearance and positions the patient connections near the display. The "backpack mounting" configuration also allows the monitor to occupy previously unused space, freeing up valuable area in the patient vicinity. The mounting for this configuration is also unique in that a single bracket can be used to mount the monitor to the display using the display mounting holes on the back of the display. In one embodiment, use of the optional handle on the display allows the "backpack mounting" configuration of the display and monitor to be articulated if mounted on a mount that supports that feature. In one embodiment, the monitor includes two brackets that allow for two monitors to be mounted behind the external display. In one embodiment, the monitor includes at least one and up to a plurality of brackets that allow for at least one and up to a plurality of monitors to be mounted behind the external display.

The monitor can be mounted directly to the wall or, in various embodiments, can be mounted on wall tracks using mounting cabinets as described below.

In one embodiment, the monitor includes a display mounting cabinet which is mounted to a standard wall track using the wall track slots. The display mounting cabinet adapts to a standard GCX wall track found in the majority of hospital installations so that new mounting holes do not need to be created. In addition, the display mounting cabinet can be powder coated to match any hospital environment. The display mounting cabinet is mounted over the wall channel and allows the mounting arm to go through the cabinet. The display mounting cabinet can be used with the external display or with the external display and monitor in the "backpack mounting" configuration described above. In another embodiment, the display mounting cabinet can support dual displays. The display mounting cabinet can house power supplies and excess cable to dress the area and make it cleaner. Removable plugs are positioned on the display mounting cabinet to allow cables to pass through. The display mounting cabinet has two separate doors to open each side. When closed, the doors are held shut by magnets. In one embodiment, cables can be stored on brackets on the outside of the display mounting cabinet as well as being stored inside. In one embodiment, the display mounting cabinet can store up to four power supplies which can be mounted in any of four locations inside the cabinet. In addition, the inside of the display cabinet contains an internal bolt pattern for brackets that allows the mounting of different items within the cabinet.

In another embodiment, the monitor includes a monitor mounting cabinet which is mounted to a standard wall track using the wall track slots. The monitor mounting cabinet adapts to a standard GCX wall track found in the majority of hospital installations and can be powder coated to match any hospital environment. The monitor mounting cabinet is mounted over the wall channel and can be mounted right side up or upside down. In addition, the monitor mounting cabinet supports reversible mounting of the monitor so that the patient parameter cables can extend from the right side or the left side of the monitor. Power for the monitor is stored within the monitor mounting cabinet and removable plugs allow for cables to pass through the cabinet.

In another embodiment, the monitor includes both a display mounting cabinet and a monitor mounting cabinet and both are mounted over a standard wall channel. In one embodiment, the monitor mounting cabinet is mounted below the display mounting cabinet. In another embodiment, the monitor mounting cabinet is mounted above the display mounting cabinet. The purpose of the mounting cabinets is to consider mounting as part of the design instead of an afterthought and to create a common integrated solution beyond just the monitor. In one embodiment, the cabinet mounting adapts to a standard GCX wall track found in the majority of hospital installations.

Module

The patient monitoring system of the present invention also includes a module which provides measurements of a plurality of patient parameters. Many types of modules exist and can be utilized, depending on which patient parameters are needed.

In one embodiment, the patient monitoring system includes a command module. The command module can measure both adult and neonatal NIBP, IBP, ECG, $SpO_2$, cardiac output, and temperature and includes a stop button to manually override NIBP measurements. The command module communicates via Synchronous Data Link Control (SDLC) bus with and derives power from the patient monitor. In addition, the command module contains internal memory to allow the module to be taken with a patient during transport and plugged into a separate monitor without losing data. In one embodiment, the command module is the core of the patient monitoring system, providing the processing power for all basic physiologic parameters. Caregivers are able to select from a variety of configurations to suit the monitoring needs of specific patients or care units in the hospital. In another embodiment, the command module includes three levels of arrhythmia monitoring (basic, standard multi-view, and advanced multi-view) as well as diagnostic 12-lead ECG analysis and reports with or without measurement and interpretation. In addition, the command module also includes ST-segment analysis and event review or Varitrend 4 for event review of neonatal respiration, heart rate, and $SpO_2$.

In one embodiment, the patient monitoring system includes a capnography module which measures the end tidal $CO_2$, minimum inspired $CO_2$, and respiratory rate to aid in evaluating the respiratory status of any adult, child, or infant patient. Routine calibrations are not required because the module automatically compensates for ambient barometric pressure. In one embodiment, the capnography module is flexible in that it combines both mainstream and sidestream monitoring modes in a single unit. Sidestream monitoring includes a low sampling rate of 50 ml/min which is ideal for smaller patients. In addition, the capnography module enables the user to obtain waveform data, numeric values (kPa, mm Hg, or %), minimum inspired $CO_2$ values, and airway respiration rates. This data can further be displayed, incorporated into trends, and/or output to charting applications.

In one embodiment, the patient monitoring system includes a Bispectral Index (BISx) module which measures depth of consciousness and sedation level of patients in operating room and critical care environments, eliminating the need for bulky standalone systems. This type of module is used to prevent patients' awareness during surgery by notifying clinicians when additional medication is needed. The BISx analysis is calculated from the frequency, power, and phase throughout the entire frequency range of the EEG and presented as an index number between 1 and 100. Adult and pediatric sensors work with the same module, which is easily moved from one monitor to another.

In one embodiment, the patient monitoring system includes a mixed Venous Oxygen Saturation ($SvO_2$) module which measures $SvO_2$ and Central Venous Oxygen Saturation ($ScvO_2$) to assess the balance of oxygen delivery and consumption. Venous oxygen saturation is being increasingly used in critically ill patients, often as part of an early goal-directed therapy protocol and in sepsis screening to aid in the assessment of cardiovascular and respiratory compromise. Catheter placement in venous monitoring is less invasive than in arterial monitoring, making it available to more patients. The $ScvO_2$ probe may be placed into an existing 16 cm or 20 cm central line, reducing or eliminating the need to exchange central venous catheters in order to provide continuous $ScvO_2$ monitoring.

In one embodiment, the patient monitoring system includes an EEG module which measures and displays brainwave activity. In one embodiment, this module also includes one channel of electromyogram (EMG) monitoring, measuring and displaying muscle electrical activity. Data storage options include two, eight, or 24 hours or snapshots. The data can be displayed as an analog moving waveform or as a density spectral array (DSA). A number of trends are available, including magnitude trends, power ratio trends, and a selection of frequency trends. Integrated electrosurgical protection assures patient safety. In one embodiment, the module is enclosed by two pieces of sheet metal.

The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be appreciated that electronic communication between devices may be effectuated by the transmission and receipt of data between applications executing in any of the devices or computing systems. Each application is configured to receive, transmit, recognize, interpret, and process such request data and information. It should further be appreciated that both the system described herein have receivers and transmitters capable of sending and transmitting data, at least one processor capable of processing programmatic instructions, memory capable of storing programmatic instructions, and software comprised of a plurality of programmatic instructions for performing the processes described herein.

FIG. 1 is a block diagram depicting one embodiment of an exemplary configuration of the components of the patient monitoring system 100, illustrating the use of DSB cables 120 to connect patient parameter measuring devices 115 to the monitor 102. In addition, in this embodiment, an external display 104 is connected to the monitor 102 by an audio/alarm light cable 113 to deliver alarm tones and nurse alert light information to the speakers and display, and by a DVI cable 114 to deliver video to the display 104. In this embodiment, one module 106 is connected to the monitor 102 via a DSB cable 116, which is directly connected to a DSB connector in the module bay (not shown).

Figure 2:
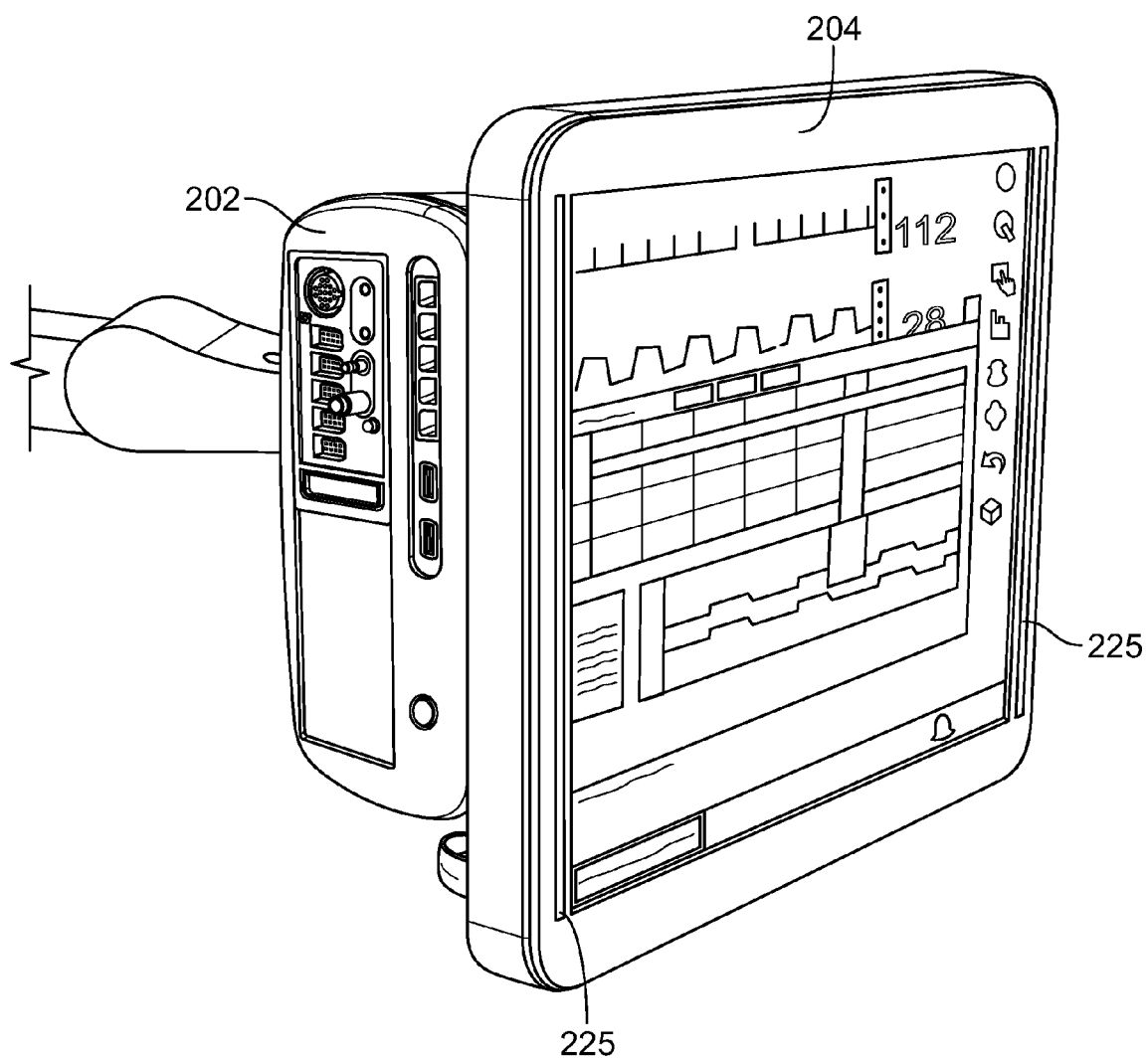
FIG. 2 is an oblique front view illustration of one embodiment of the patient monitoring system depicting a monitor and external display with red alarm lights on the front of the display.

FIG. 2 is an oblique front view illustration of one embodiment of the patient monitoring system depicting a monitor 202 and external display 204 with red alarm lights 225 on the front of the display 204. In one embodiment, the glass is treated such that it allows the transmitted light to pass through. In one embodiment, a black border is silk-screened on the back of the glass around the perimeter. In one embodiment, the black border is comprised of an ink that is silk-screened or sprayed onto a masked out border area that gives the appearance of a continuous and uniform black border but allows light to pass through when the alarm is sounded, yielding a visual alarm. Thus, the black border of the display 204 appears uniform and continuous until an alarm occurs. Once an alarm is activated, a light source built into the body of the display 204 transmits light in an appropriate wavelength to the glass covering the front of the display 204 to indicate alarms.

In another embodiment, the glass contains small apertures that allow the transmitted light to pass through.

Referring to FIG. 2, a red light 225 is seen on both sides of the front of the display 204. In this embodiment, a red light signifies a high priority alarm. The display is also capable of transmitting a yellow light signifying a medium priority alarm and a cyan light signifying a low priority alarm.

Figure 3A:
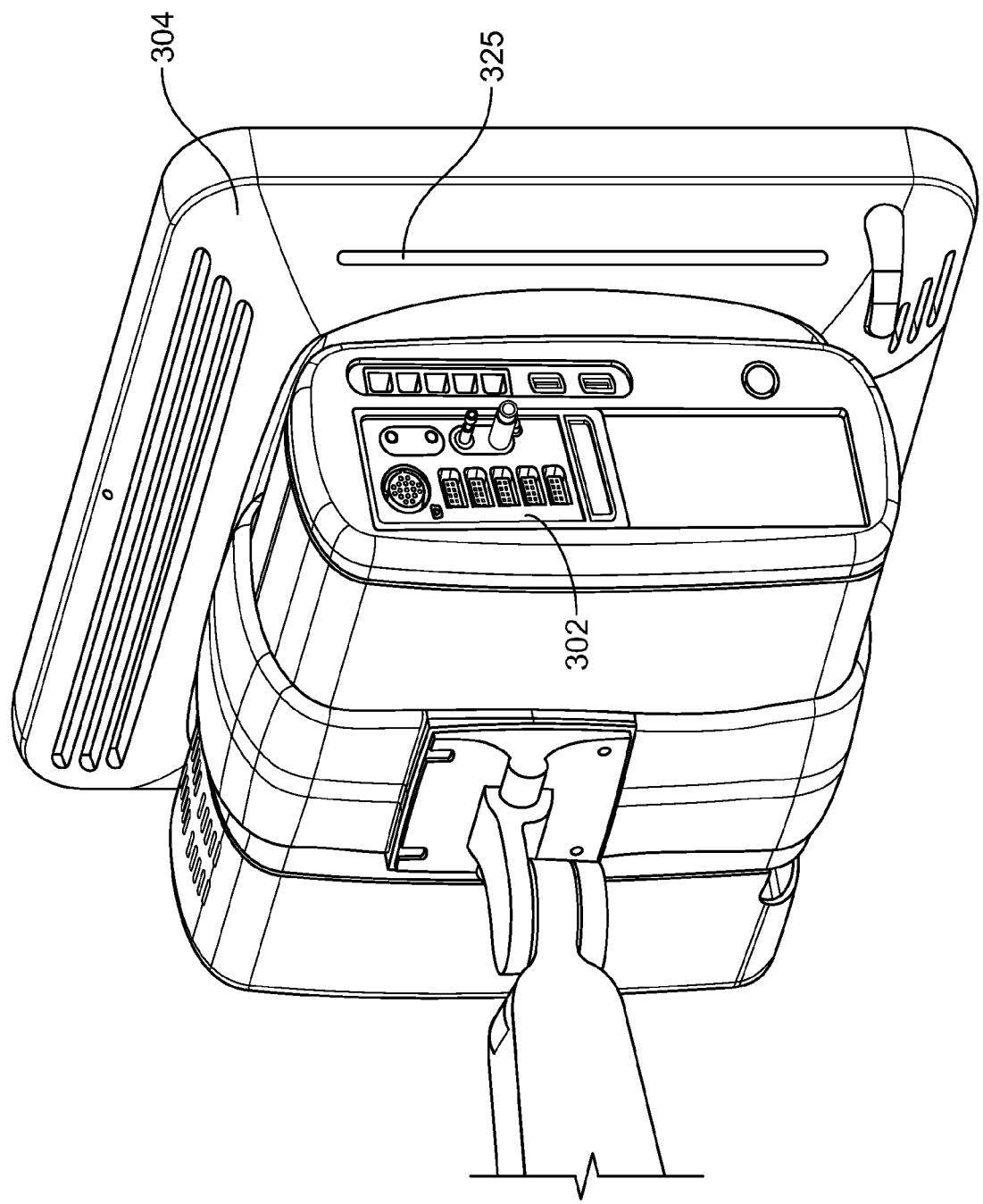
FIG. 3A is an oblique rear view illustration of one embodiment of the patient monitoring system depicting a monitor and external display with red alarm lights on the back of the display.

FIG. 3a is an oblique rear view illustration of one embodiment of the patient monitoring system depicting a monitor 302 and external display 304 with red alarm lights 325 on the back of the display 304. In one embodiment, openings for these alarm lights are molded into the rear display enclosure. In one embodiment, at least one opening is insert-molded into the left side and right side of the rear enclosure. In one embodiment, the openings are in the form of slots that extend vertically along the surface of the rear enclosure. In one embodiment, the slots measure 0.25 inches wide by 9 inches long. In other embodiments, the slots measure from at least 0.10 to 1.0 inches wide and from 1.0 to 10.0 inches long. In other various embodiments, the openings are in the form of circles, squares, or any other shape that allows for alarm visualization. In one embodiment, the openings are offset from the front touchscreen of the display by 1.9 inches. In other embodiments, the openings are offset from the front touchscreen of the display by 1.0 to 2.0 inches.

In FIG. 3a, a red alarm light 325 can be seen on the right rear side of the display 304. Though not visible in this figure, an additional red alarm light is positioned on the left rear side of the display 304. These alarm lights are visible to medical personnel from the side or rear of the patient monitoring system, and, when considered together with the front alarm lights, allow the user to view alarm lights from a full 360 degrees around the display 304.

Figure 3B:
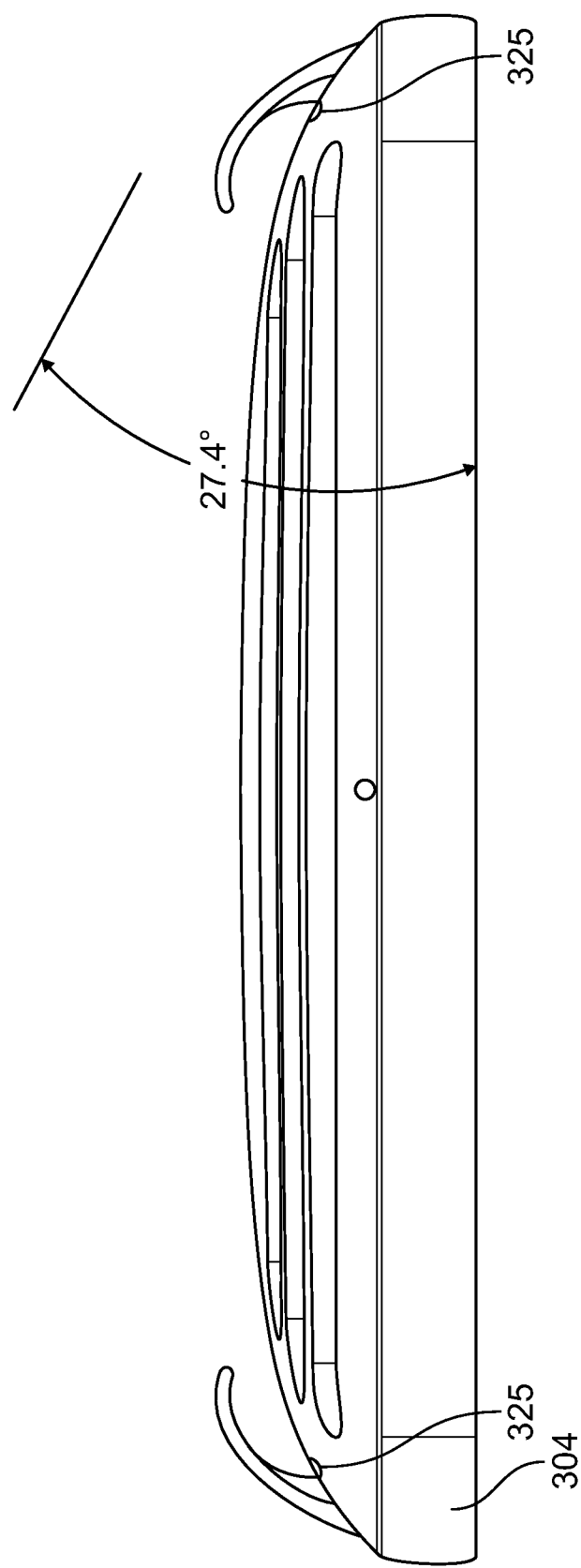
FIG. 3B is a top down view illustration of one embodiment of the patient monitoring system depicting openings for the side alarms of an external display offset at a particular angle with respect to the front of said display.

FIG. 3b is a top down view illustration of one embodiment of the patient monitoring system depicting openings for the side alarms 325 of an external display 304 offset at a particular angle with respect to the front of said display. In one embodiment, the openings for the side alarms are offset from the plane of the front of the display by an angle of 27.4 degrees. In other embodiments, the openings for the side alarms are offset from the plane of the front of the display by an angle of 15 to 45 degrees.

Figure 3C:
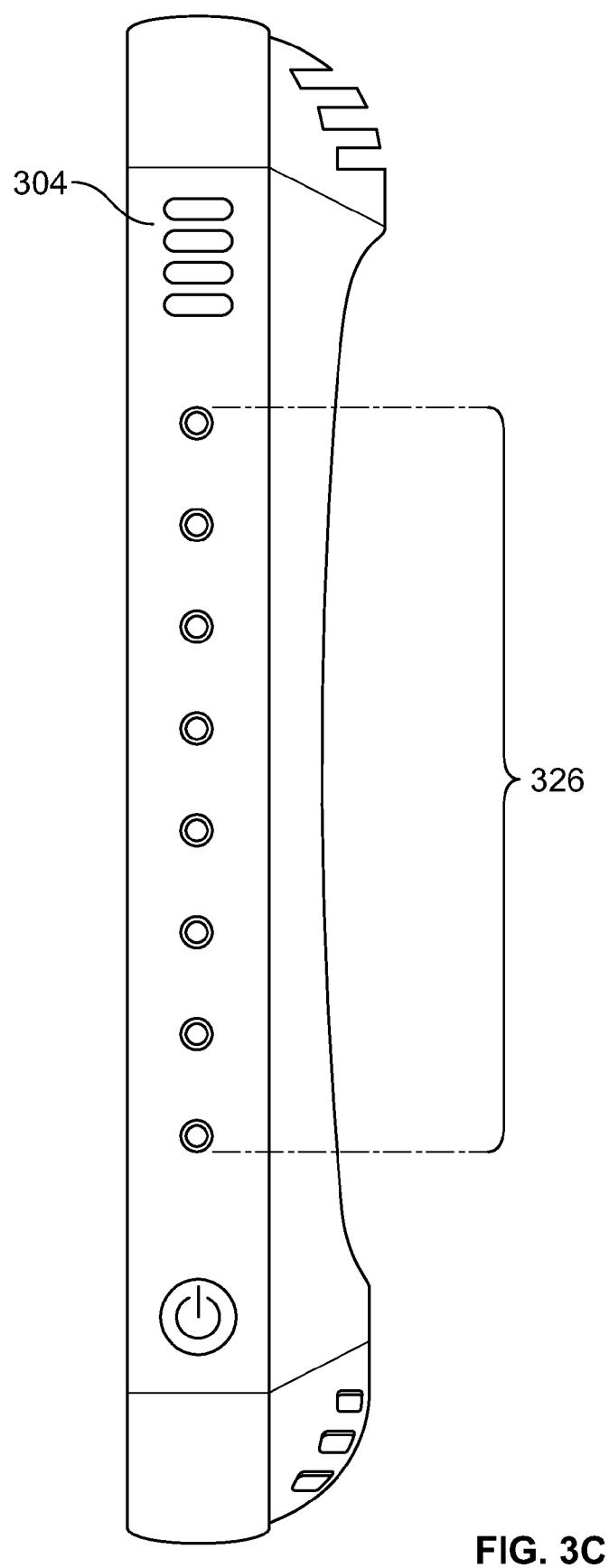
FIG. 3C is a side view illustration of one embodiment of an external display depicting a column of small apertures positioned on the side edge of the display.

FIG. 3c is a side view illustration of another embodiment of an external display 304 depicting a column of small apertures 326 positioned on the side edge of said display 304. In this embodiment, light emitted from an internal source passes through these small apertures 326 during an alarm situation. Though not visible in this figure, an identical set of apertures is located on the opposite side of the display. Passage of light through these apertures 326 allows medical personnel to view visual alarm lights from both sides of the external display 304.

Figure 4:
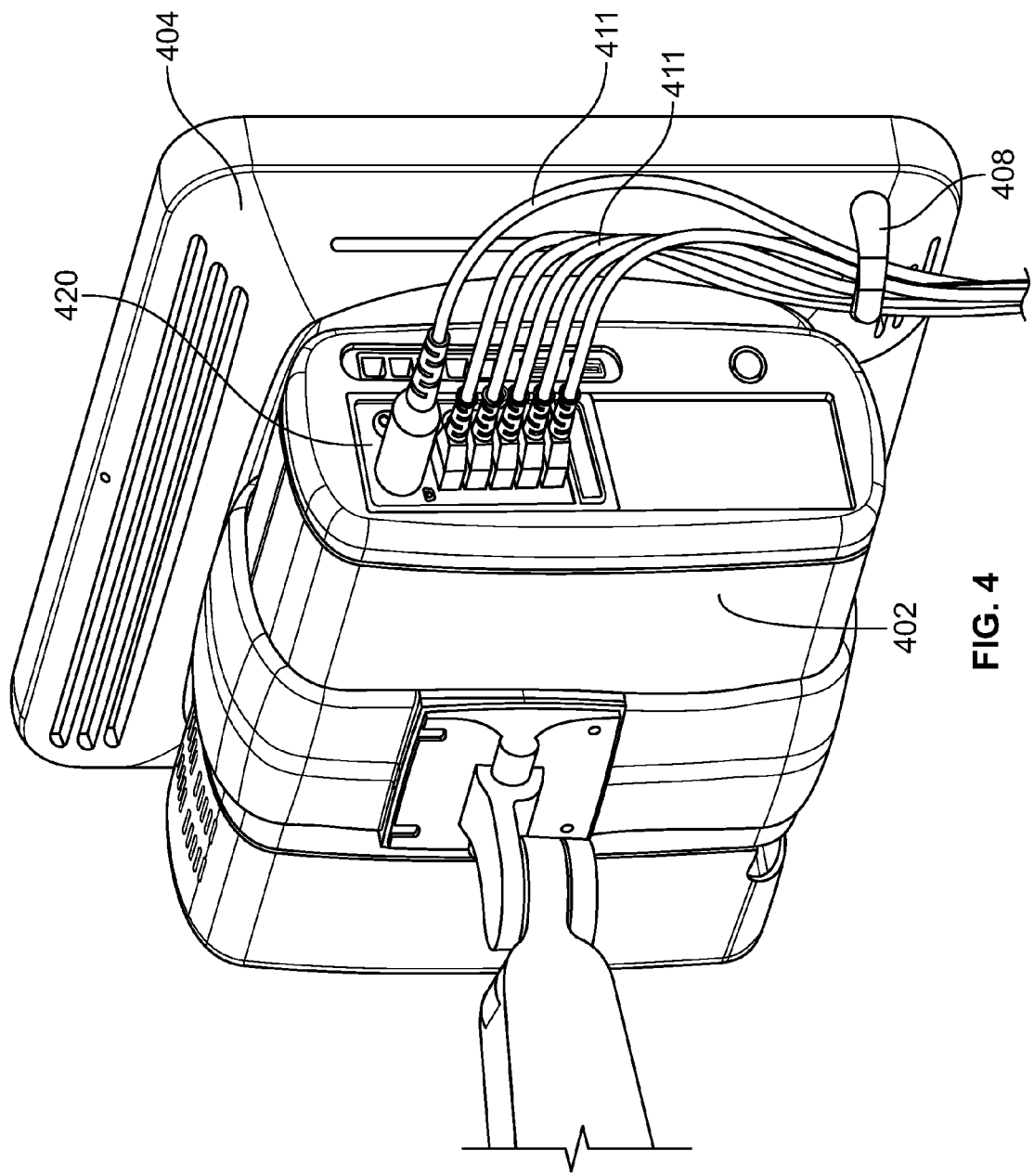
FIG. 4 is an oblique rear view illustration of one embodiment of the patient monitoring system depicting a monitor and external display with optional integrated cable hooks on the rear display enclosure and a plurality of cables passing through one cable hook and plugging into an inserted module.

FIG. 4 is an oblique rear view illustration of one embodiment of the patient monitoring system depicting a monitor 402 and external display 404 with optional integrated cable hooks 408 on the rear display enclosure and a multitude of cables 411 passing through one cable hook 408 and plugging into the an inserted module 420. Though not visible on this figure, an identical cable hook is located on the left rear side of the display 404. The cable hooks assist in routing cables. In one embodiment, the cable hooks are composed of a flexible material that will not mar cables and will bend and flex to allow passage of a greater number of cables. In one embodiment, the cable hooks affix to the display by snapping into the rear display enclosure. In the pictured embodiment, the cable hooks 408 are mounted in a horizontal position. In another embodiment, the cables hooks are mounted in a vertical position.

Figure 5:
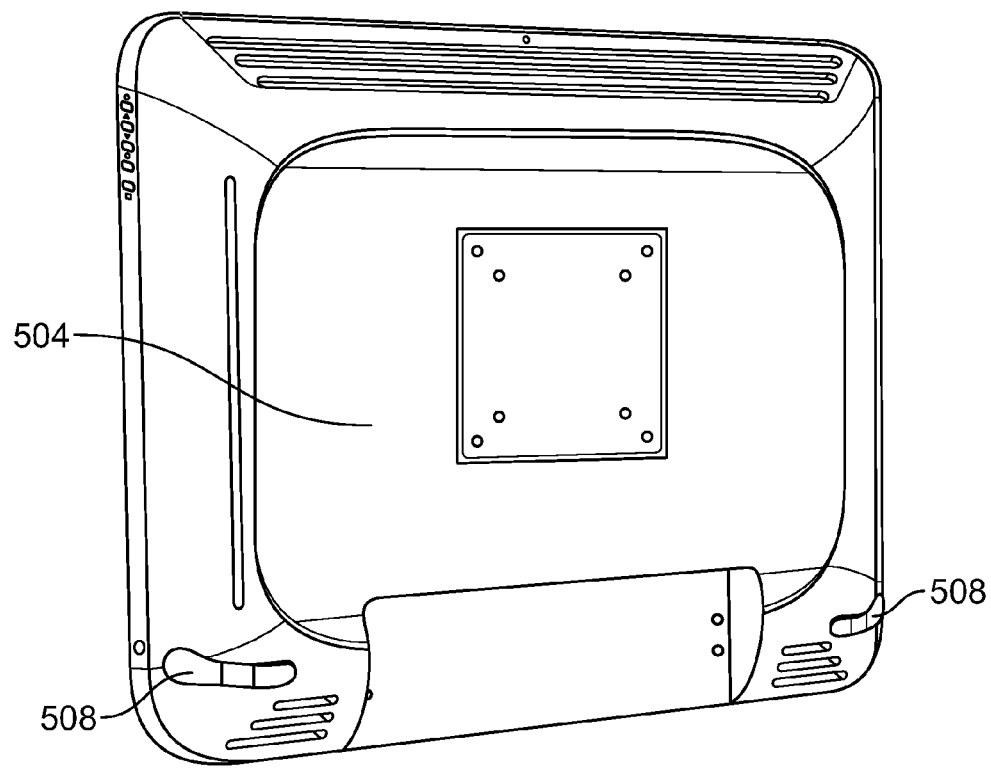
FIG. 5 is an oblique rear view illustration of one embodiment of the external display of the patient monitoring system, depicting optional integrated cable hooks on the rear display enclosure.

FIG. 5 is an oblique rear view illustration of one embodiment of the external display 504 of the patient monitoring system, depicting optional integrated cable hooks 508 on the rear display enclosure. In this figure, both cable hooks 508 can be seen and are mounted in the horizontal position.

Figure 6:
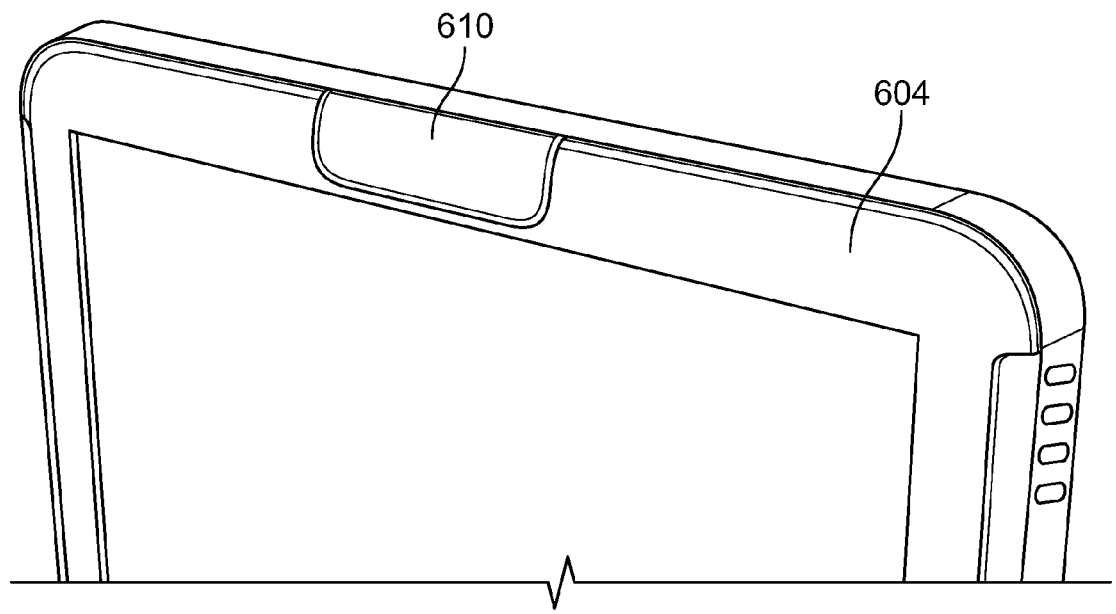
FIG. 6 is an oblique front view illustration of one embodiment of the external display of the patient monitoring system, depicting a large programmable touch button positioned on the upper edge of the front of the display.

FIG. 6 is an oblique front view illustration of one embodiment of the external display 604 of the patient monitoring system, depicting a large programmable touch button 610 positioned on the upper edge of the front of the display 604. As can be seen in the figure, the touch button 610 is large and is situated prominently along the upper edge of the front of the display. This makes the button 610 easy to find when a nurse needs to silence an alarm, reset alarm indicators, and tend to patient needs. In one embodiment, the button is programmed to silence alarms. In another embodiment, the button is programmed to initiate NIBP readings. In other various embodiments, the button can be programmed to serve other medical personnel needs. In other various embodiments, the button can be located on any other part of the edge of the front of the display, as long as it remains both large and prominent. In various embodiments, the button is a metal plate or other conductive material utilizing any commonly used touch and/or pressure sensitive technologies.

Figure 7:
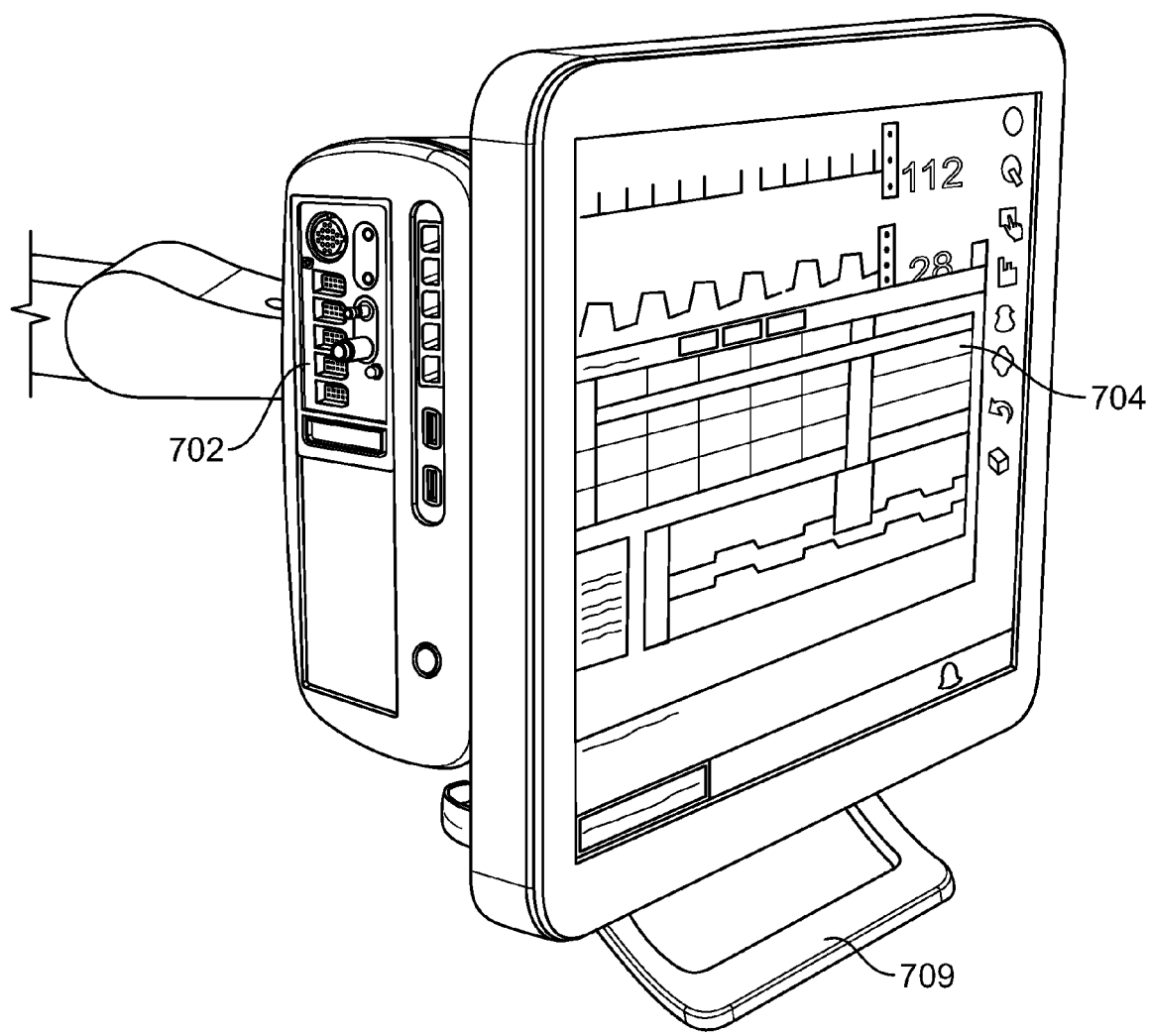
FIG. 7 is an oblique front view illustration of one embodiment of the patient monitoring system depicting a monitor and external display with an optional handle extending from the bottom of the display.

FIG. 7 is an oblique front view illustration of one embodiment of the patient monitoring system depicting a monitor 702 and external display 704 with an optional handle 709 extending from the bottom of the display 704. In one embodiment, the optional handle 709 is mounted to the rear display enclosure and extends both downwards and forwards from the bottom of the display 704. The optional handle 709 assists in one-handed manipulation of the patient monitoring system by medical personnel. This leaves them free to assist with patient needs with their free hand.

Figure 8:
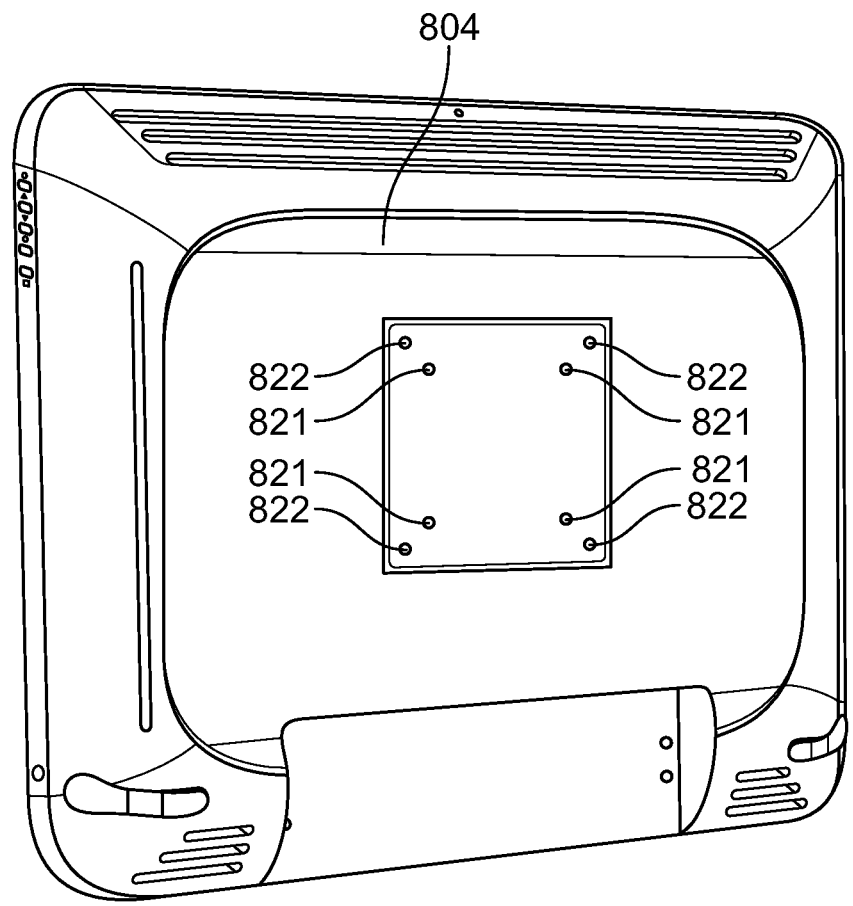
FIG. 8 is an oblique rear view illustration of one embodiment of the external display of the patient monitoring system, depicting two hole patterns for mounting of the external display to standard mounts.

FIG. 8 is an oblique rear view illustration of one embodiment of the external display 804 of the patient monitoring system, depicting two hole patterns 821, 822 for mounting of the external display 804 to standard mounts. The set of holes 822 farther from the center of the rear of the display 804 are for standard 100 mm VESA mounts and the holes 821 nearer the center of the rear of the display 804 are for standard 75 mm VESA mounts. Either set of holes may be used depending upon which mounts are available in the hospital.

Figure 9:
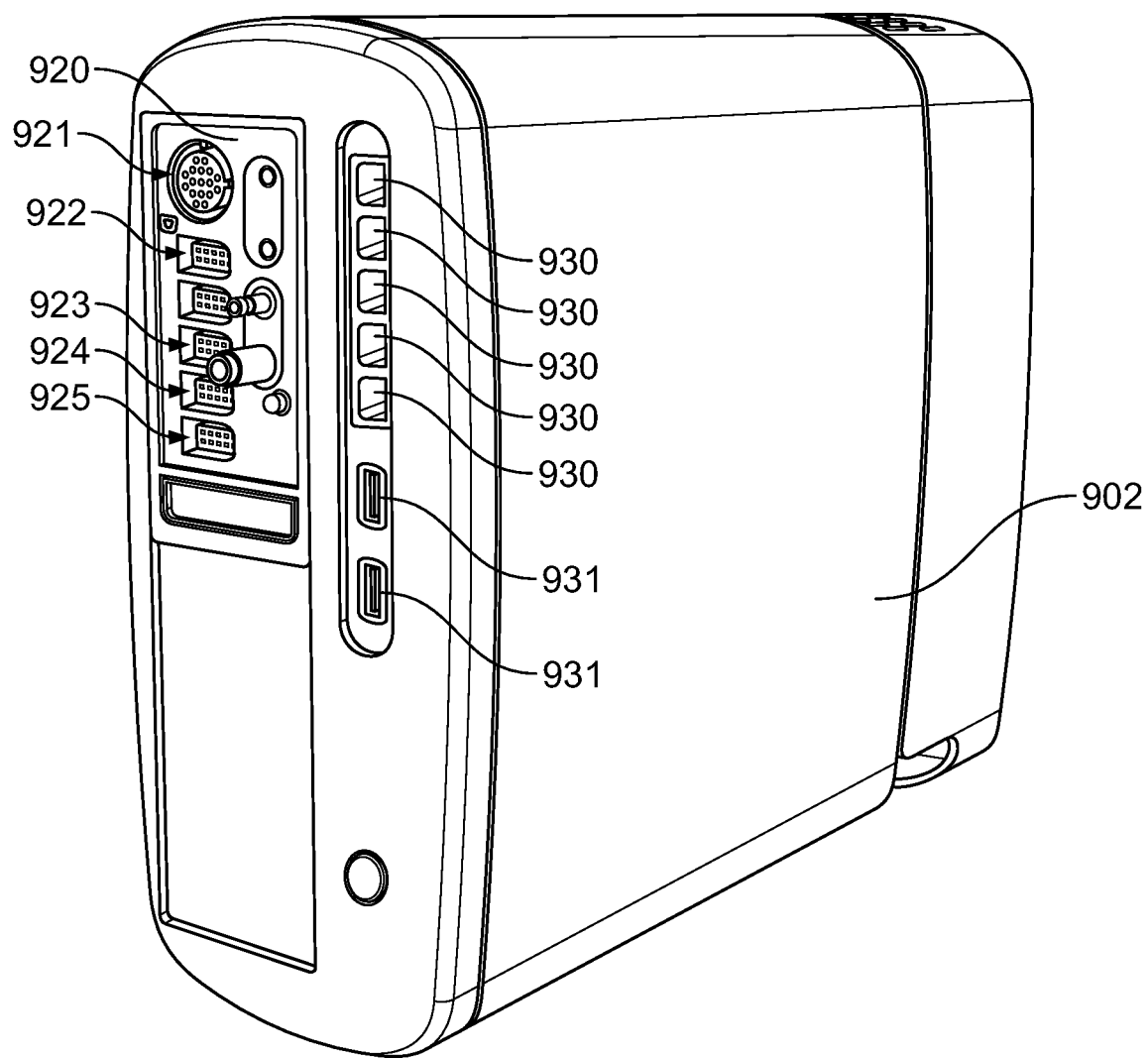
FIG. 9 is an oblique front view illustration of one embodiment of the monitor of the patient monitoring system with a module inserted therein, depicting a plurality of receptacles on the front of the module available for inputs from other system components.

FIG. 9 is an oblique front view illustration of one embodiment of the monitor 902 of the patient monitoring system with a module 920 inserted therein, depicting a multitude of receptacles on the front of the module 920 available for inputs from other system components. In one embodiment, the receptacles include an ECG component port 921, IBP component port 922, SPO₂ component port 923, CO component port 924, and temperature component port 925. In this embodiment, the monitor 902 contains five DSB ports 930 to allow for connection to smart cable parameters (patient parameter measuring devices). In addition, USB ports 931 are provided to connect compatible peripheral devices.

Figure 10:
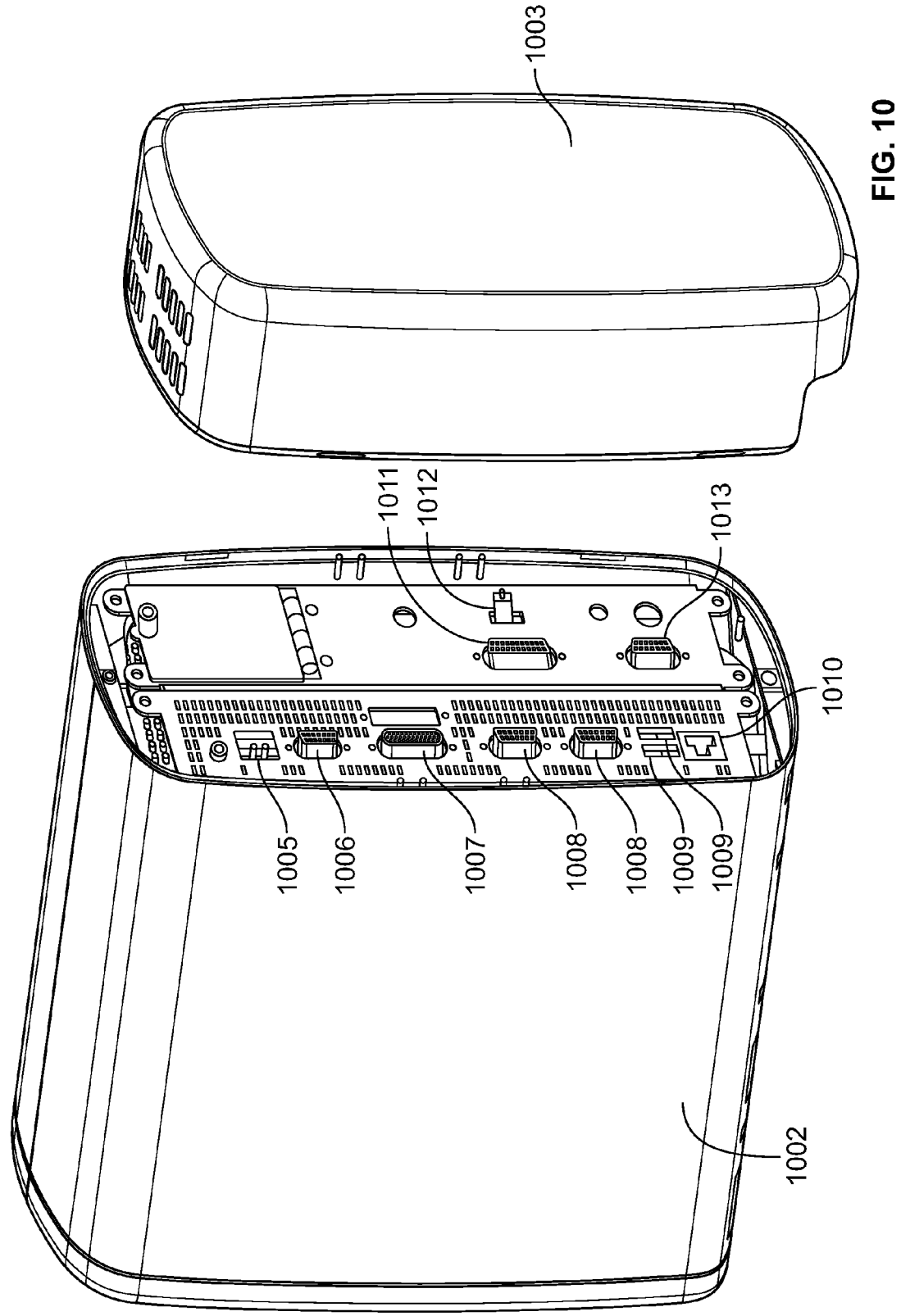
FIG. 10 is an oblique rear view illustration of one embodiment of the monitor of the patient monitoring system, depicting a removable monitor cable cover and a multitude of receptacles on the back of the monitor available for other system component inputs and an optional printer.
Figure 11:
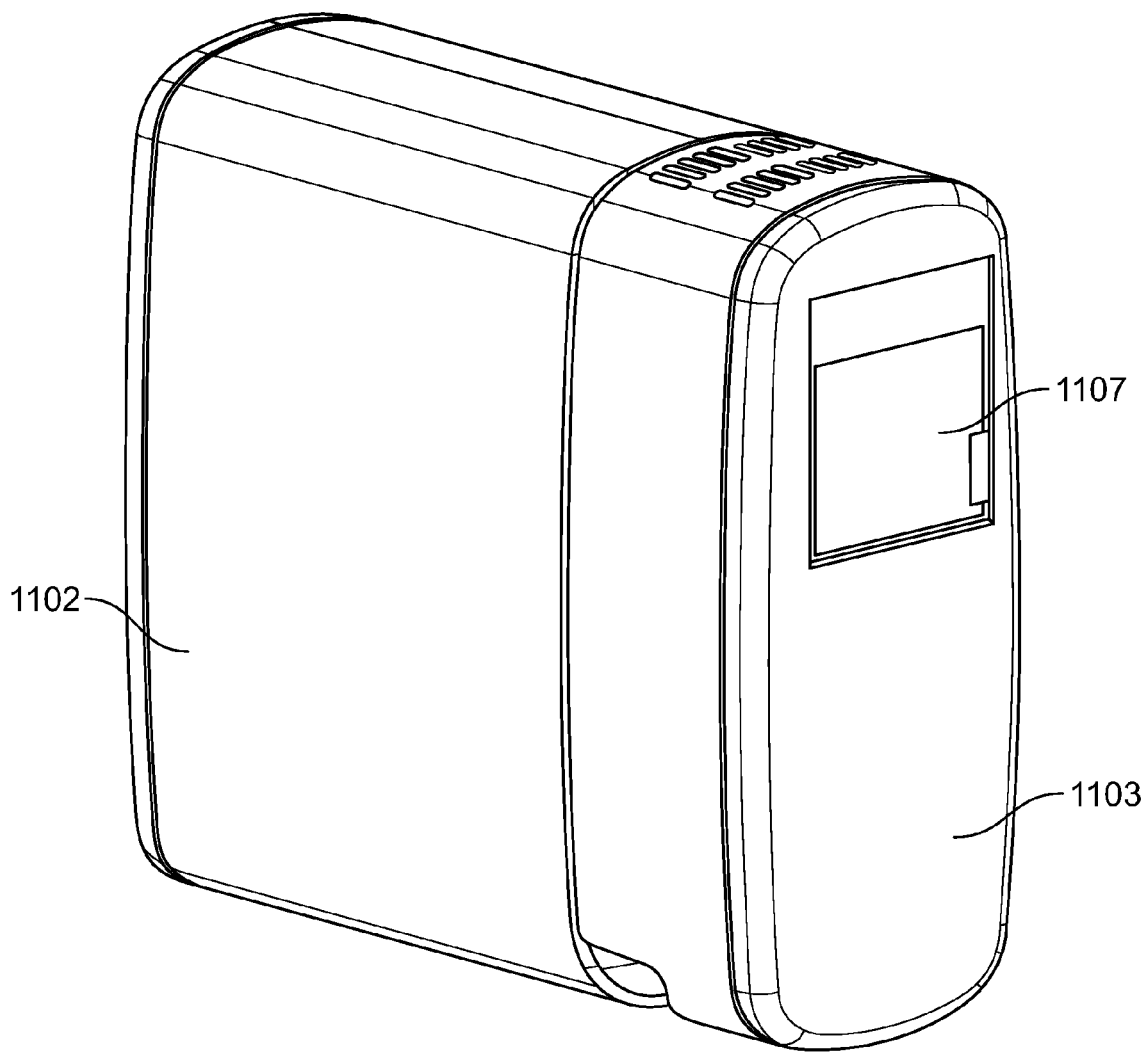
FIG. 11 is an oblique rear view illustration of one embodiment of the monitor of the patient monitoring system, depicting a removable monitor cable cover with integrated thermal printer attached to the back of the monitor.

FIG. 10 is an oblique rear view illustration of one embodiment of the monitor 1002 of the patient monitoring system, depicting a removable monitor cable cover 1003 and a multitude of receptacles on the back of the monitor 1002 available for other system component inputs and an optional printer, shown in FIG. 11. In one embodiment, the receptacles include external alarm light connection 1005, external nurse alert/external audio/IR receiver connection 1006, DVI video output 1007 (may include two where dual display is supported), serial ports 1008 (for data logging, programming), USB ports 1009, Ethernet connection 1010, synchronous data link control (SDLC) serial port 1011 and SDLC termination switch 1012, and high level out port 1013.

In one embodiment, the monitor cable cover 1003 is tethered to the monitor 1002 so it cannot be lost. In one embodiment, the monitor cable cover 1003 includes a thermal printer to expand the capabilities of the monitor. In one embodiment, the printer accepts 50 mm paper.

FIG. 11 is an oblique rear view illustration of one embodiment of the monitor 1102 of the patient monitoring system, depicting a removable monitor cable cover 1103 with integrated thermal printer 1107 attached to the back of the monitor 1102.

Figure 12:
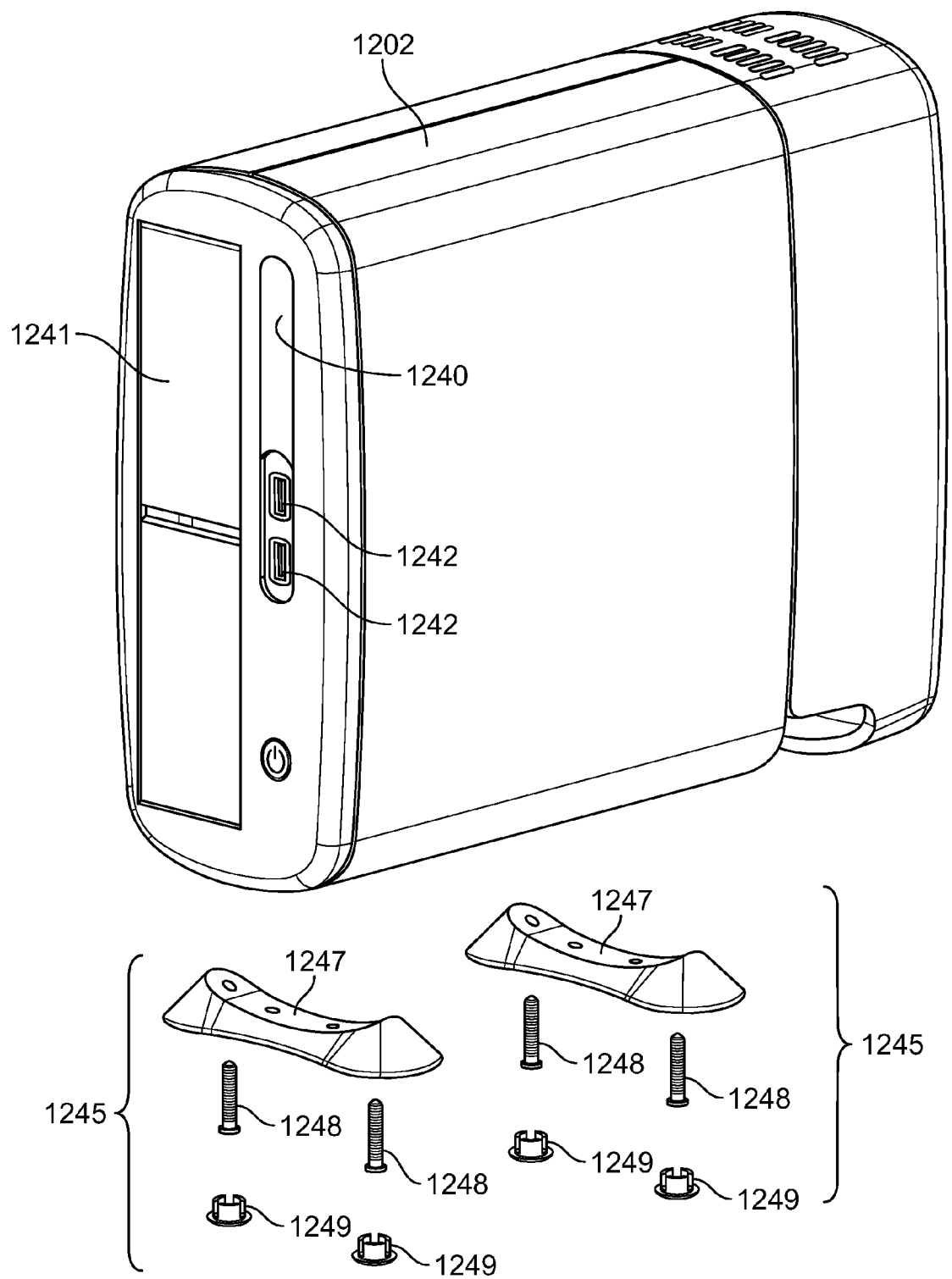
FIG. 12 is an oblique front view illustration of one embodiment of the monitor of the patient monitoring system, depicting receptacle covers in place over the connectors on the front of the monitor, and optional foot mounts for standing the monitor on a level surface.

FIG. 12 is an oblique front view illustration of one embodiment of the monitor 1202 of the patient monitoring system, depicting receptacle cover 1240 in place over the connectors on the front of the monitor 1202, module slot door 1241, and optional foot mounts 1245 for standing the monitor 1202 on a level surface. In one embodiment, there is a separate cover 1240 for the five DSB connectors and a separate door 1241 covering the module slot. In one embodiment, two receptacles 1242 remain uncovered and are normal USB ports. When in place, the receptacle covers give the monitor an overall cleaner look and also prevent the deposition of unwanted materials, including but not limited to, dust, debris, and liquids, into the connectors. In one embodiment, the monitor 1202 includes two foot support mounts 1245. In one embodiment, the two foot support mounts 1245 are installed into the bottom of the monitor 1202 and each include one foot support 1247, two installation screws 1248, and two screw covers 1249. The screw covers 1249 are made of a softer material and grip the table top to prevent sliding along a surface. The optional foot supports 1245 lend the monitor 1202 extra stability when the monitor 1202 is stood upon a level surface and assist in preventing the monitor 1202 from falling over if inadvertently touched, pushed, or pulled. In one embodiment, the optional foot also includes center holes to allow for the monitor to be bolted to the surface from the underside without having to remove the feet.

Figure 13:
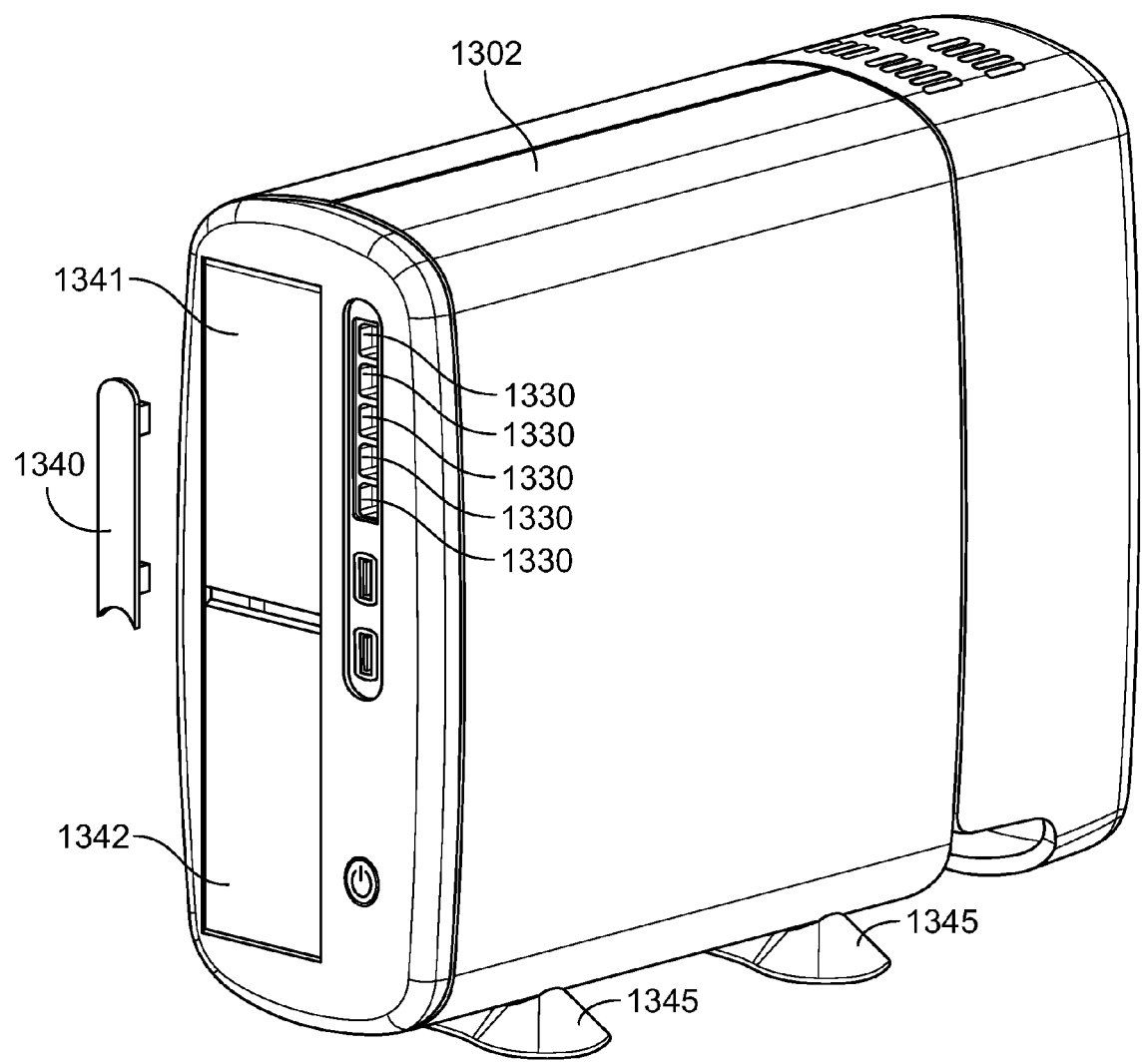
FIG. 13 is an oblique front view illustration of one embodiment of the monitor of the patient monitoring system, depicting doors in place and receptacle cover removed from the DSB connectors on the front of the monitor, and installed optional foot mounts for standing the monitor on a level surface.

FIG. 13 is an oblique front view illustration of one embodiment of the monitor 1302 of the patient monitoring system, depicting doors 1341, 1342 in place and receptacle cover 1340 removed from the DSB connectors on the front of the monitor 1302, and installed optional foot mounts 1345 for standing the monitor on a level surface. The receptacle cover 1340 for the DSB connectors 1330 is not in place and can be seen to the left of the monitor 1302. Door 1341 is in place over a first module slot, and is a door that covers the module housing when no module is installed. A second door 1342 covers an additional module slot directly below the first. Each door is spring loaded and automatically closed when there is no module and is opened when a module pushes in against it. In one embodiment, each module bay measures 3.0 inches wide×5.0 inches high×9.5 inches deep. In other embodiments, each module bay measures from 2.5 to 3.5 inches wide×4.0 to 6.0 inches high×8.5 to 10.5 inches deep, based on the size of the module to be inserted. Two optional foot supports 1345 are installed into the bottom of the monitor 1302.

Figure 14A:
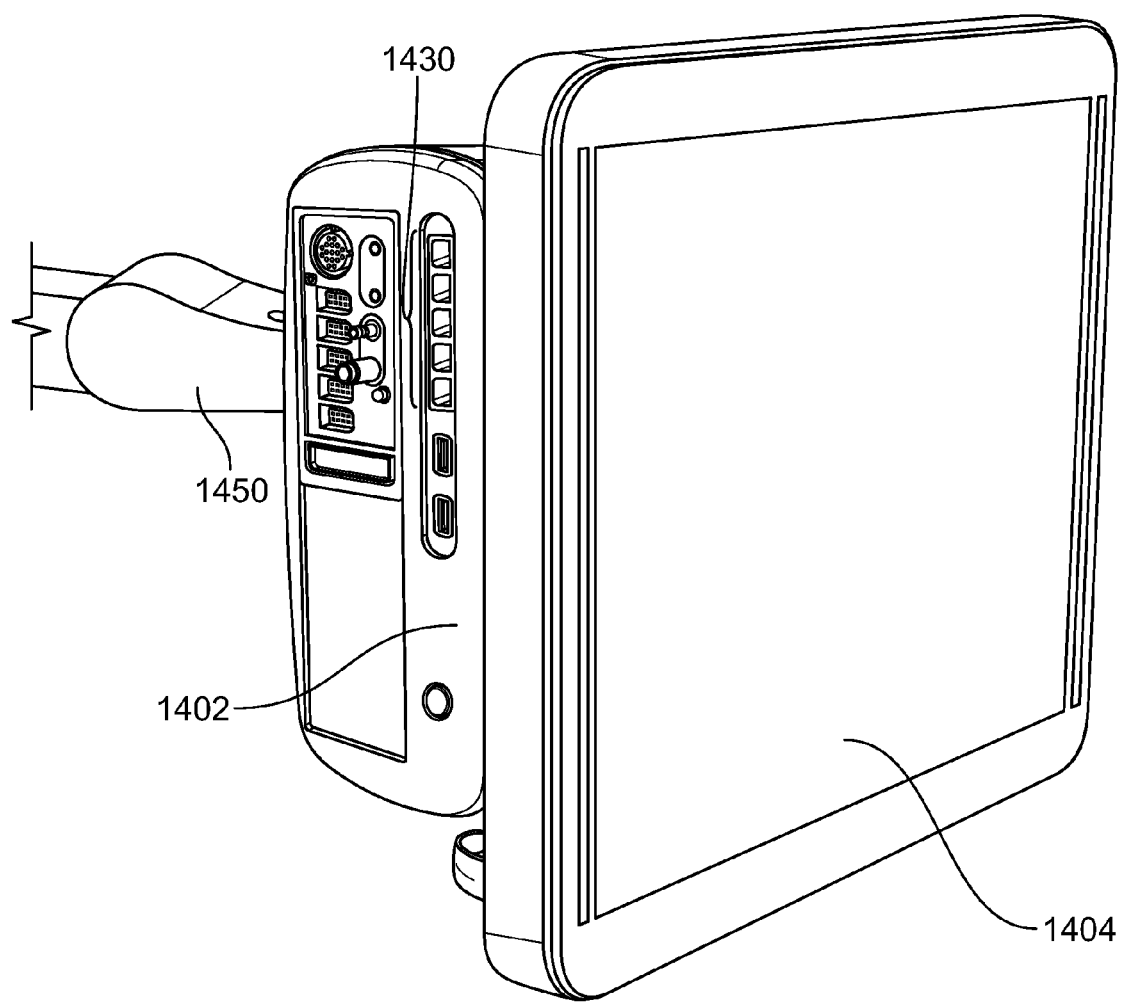
FIG. 14A is an oblique front view illustration of one embodiment of the monitor and external display connected together in the "backpack mounting" configuration and attached to a support arm.

FIG. 14*a* is an oblique front view illustration of one embodiment of the monitor 1402 and external display 1404 connected together in the "backpack mounting" configuration and attached to a support arm 1450. In one embodiment, the display 1404 measures 17.7 inches wide×14.9 inches high×2.6 inches thick. In other embodiments, the display 1404 measures from 16.2 to 19.2 inches wide×13.6 to 16.2 inches high×2.0 to 3.2 inches thick. In one embodiment, the monitor 1402 measures 13.0 inches wide×11.0 inches high×4.8 inches thick. In other embodiments, the monitor 1402 measures from 11.5 to 14.5 inches wide×9.7 to 12.3 inches high×4.2 to 5.4 inches thick. All of the above measurements allow for 'backpack mounting' of the monitor 1402 to the display 1404.

The back of the display 1404 is contoured to "nest" the monitor 1402 so that when attached together they appear to be one unit. This gives the system a cleaner look and also frees up valuable space around the patient bed. The "backpack mounting" feature enables reversible connection of the monitor 1402 to the display 1404. In this embodiment, the monitor 1402 is attached to the display 1404 so that the DSB connectors 1430 and other receptacles located on the front of the monitor 1402 are positioned toward the left side of the display 1404 when viewed from the front. This allows for the patient cables and USB devices that are attached to the system to extend from the left side.

Figure 14B:
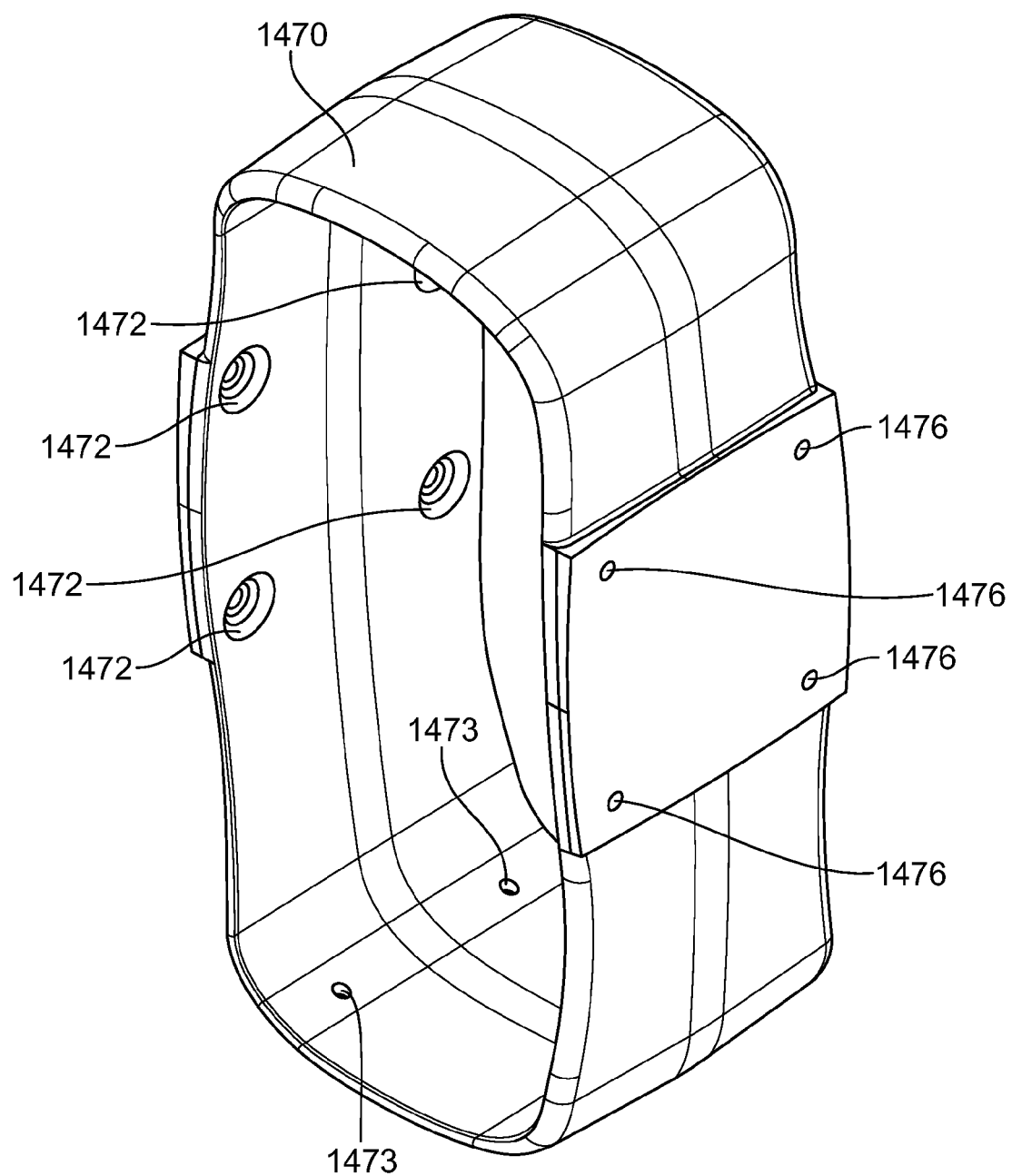
FIG. 14B is an oblique front view illustration of one embodiment of a bracket used to connect the monitor to the display in the "backpack mounting" configuration.
Figure 14C:
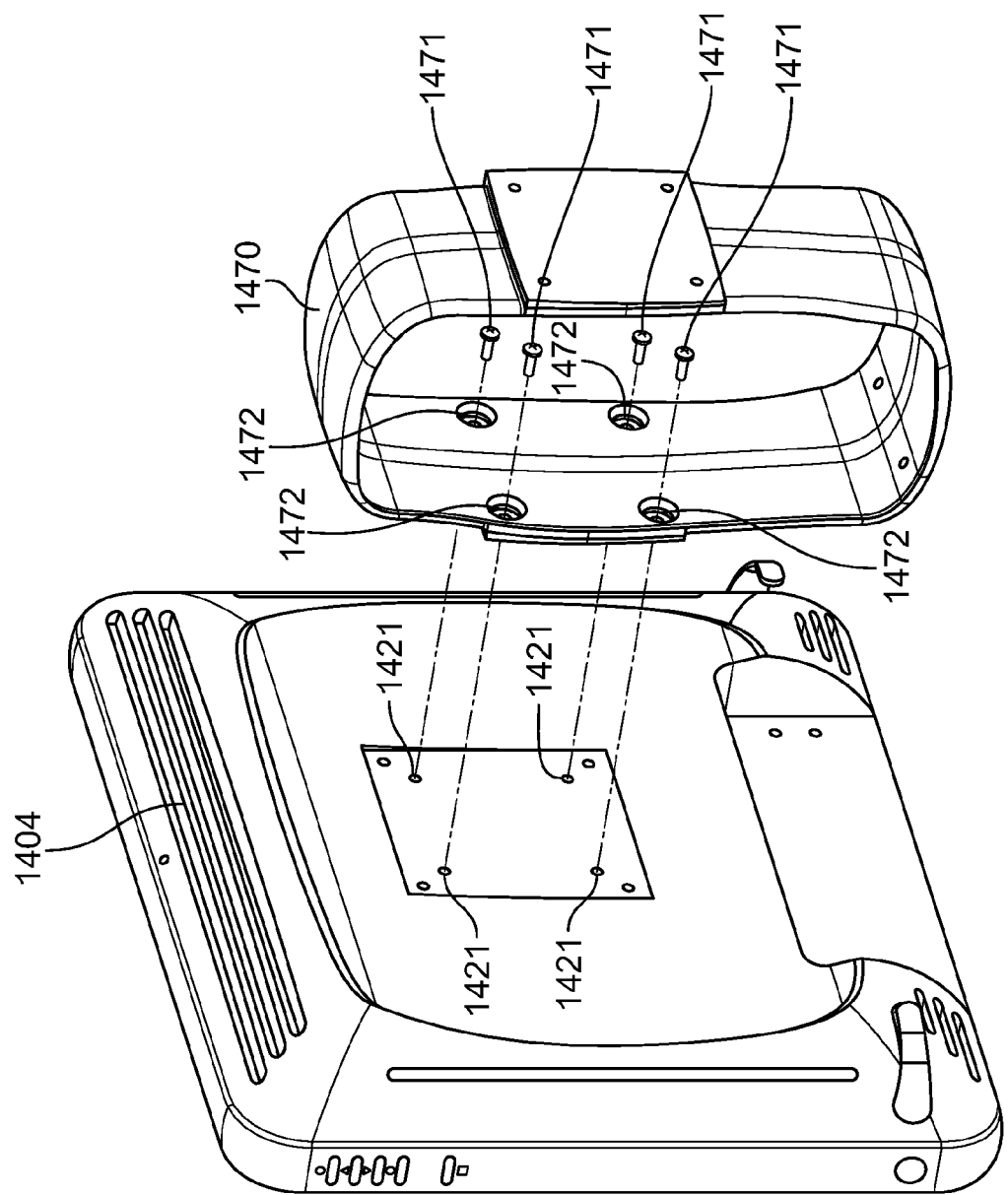
FIG. 14C is an oblique rear view illustration of one embodiment of a display of the patient monitoring system, depicting the attachment of a bracket used for "backpack mounting"

FIG. 14*b* is an oblique front view illustration of one embodiment of a bracket 1470 used to connect the monitor to the display in the "backpack mounting" configuration. In one embodiment, the bracket 1470 is formed in the shape of an oval. In various other embodiments, the bracket is formed in the shape of a rectangle, square, or any other shaped based on the shape of the monitor. In one embodiment, on a first side of the bracket 1470, said bracket 1470 includes four mounting holes 1472 for mounting the bracket 1470 to the display. The mounting holes 1472 are arranged to match a hole pattern on the back of the display. In one embodiment, the mounting holes 1472 are arranged for a standard 75 mm VESA pattern. In another embodiment, the mounting holes 1472 are arranged for a standard 100 mm VESA pattern. On a second side opposite the first side of the bracket 1470, the bracket 1470 includes four mounting holes 1476 for mounting the bracket 1470 to a flexible mounting arm. The mounting holes 1476 are arranged to match a hole pattern present on traditional hospital based wall track mounting arms. Additionally, the bracket 1470 includes, at the bottom of said bracket 1470, four mounting holes 1473 (only two are visible in FIG. 14*b*) for securing the monitor to the bracket 1470 once the monitor has been slid into position within said bracket 1470. FIG. 14*c* is an oblique rear view illustration of one embodiment of a display 1404 of the patient monitoring system, depicting the attachment of a bracket 1470 used for "backpack mounting". Four screws 1471 are inserted into the mounting holes 1472 and screwed into the holes 1421 set into the back of the display 1404. In the depicted embodiment, the mounting holes 1472 in the bracket 1470 and the holes in the back of the display 1421 are set in a standard 75 mm VESA pattern. In another embodiment, the mounting holes 1472 in the bracket 1470 and the holes in the back of the display 1421 are set in a standard 100 mm VESA pattern.

Figure 14D:
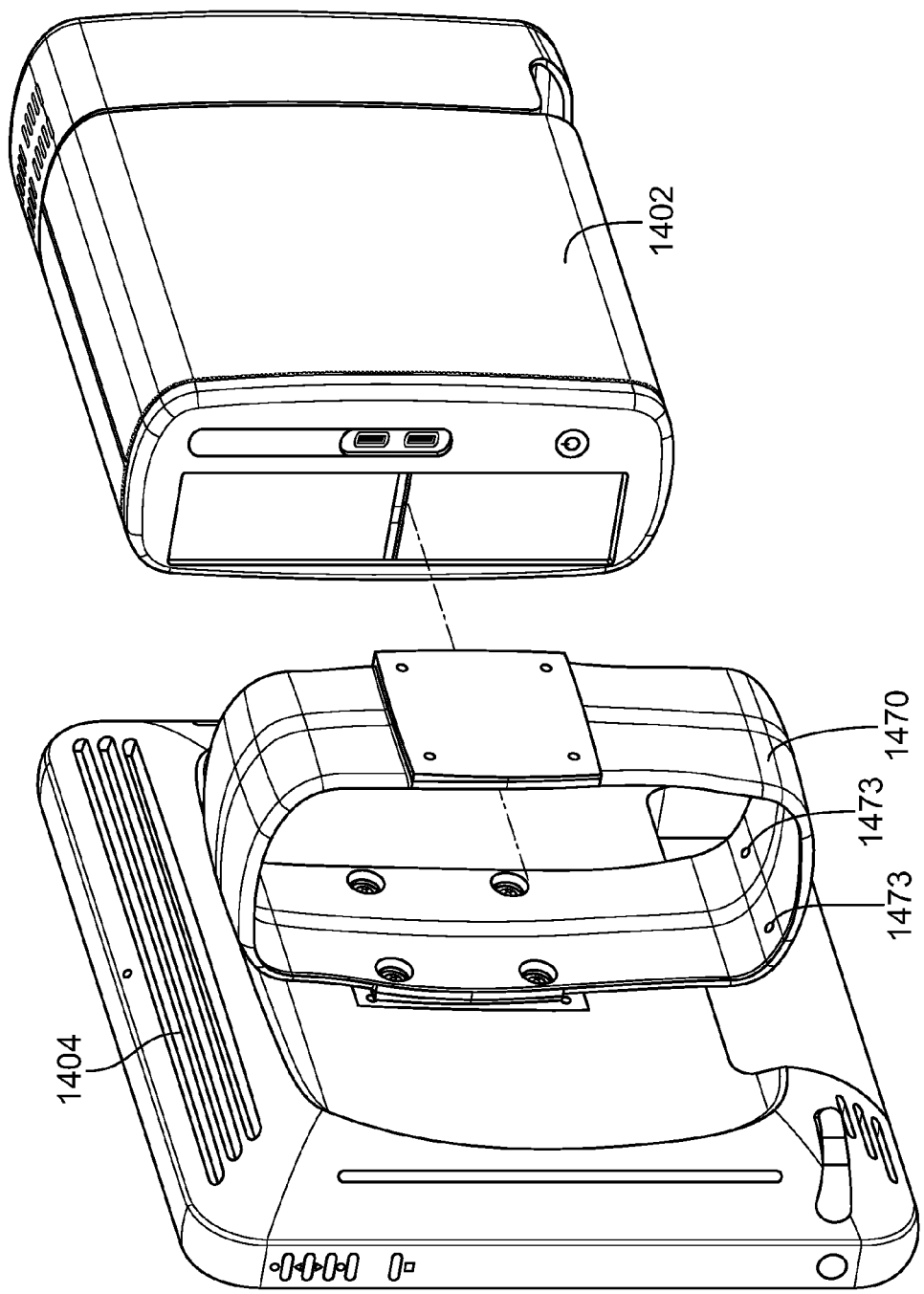
FIG. 14D is an oblique rear view illustration of one embodiment of a display with an attached bracket, depicting the insertion of a monitor into the bracket for "backpack mounting"

FIG. 14d is an oblique rear view illustration of one embodiment of a display 1404 with an attached bracket 1470, depicting the insertion of a monitor 1402 into the bracket 1470 for "backpack mounting". The monitor 1402 is slid into the bracket 1470 from either side of said bracket 1470 and is then secured to the bracket 1470 via four mounting holes 1473 (only two are visible in FIG. 14d) located at the bottom of said bracket. The monitor 1402 can be slid into the bracket 1470 from either side of the bracket 1470 and can be oriented to face toward either the left or right side of the display 1404.

Figure 14E:
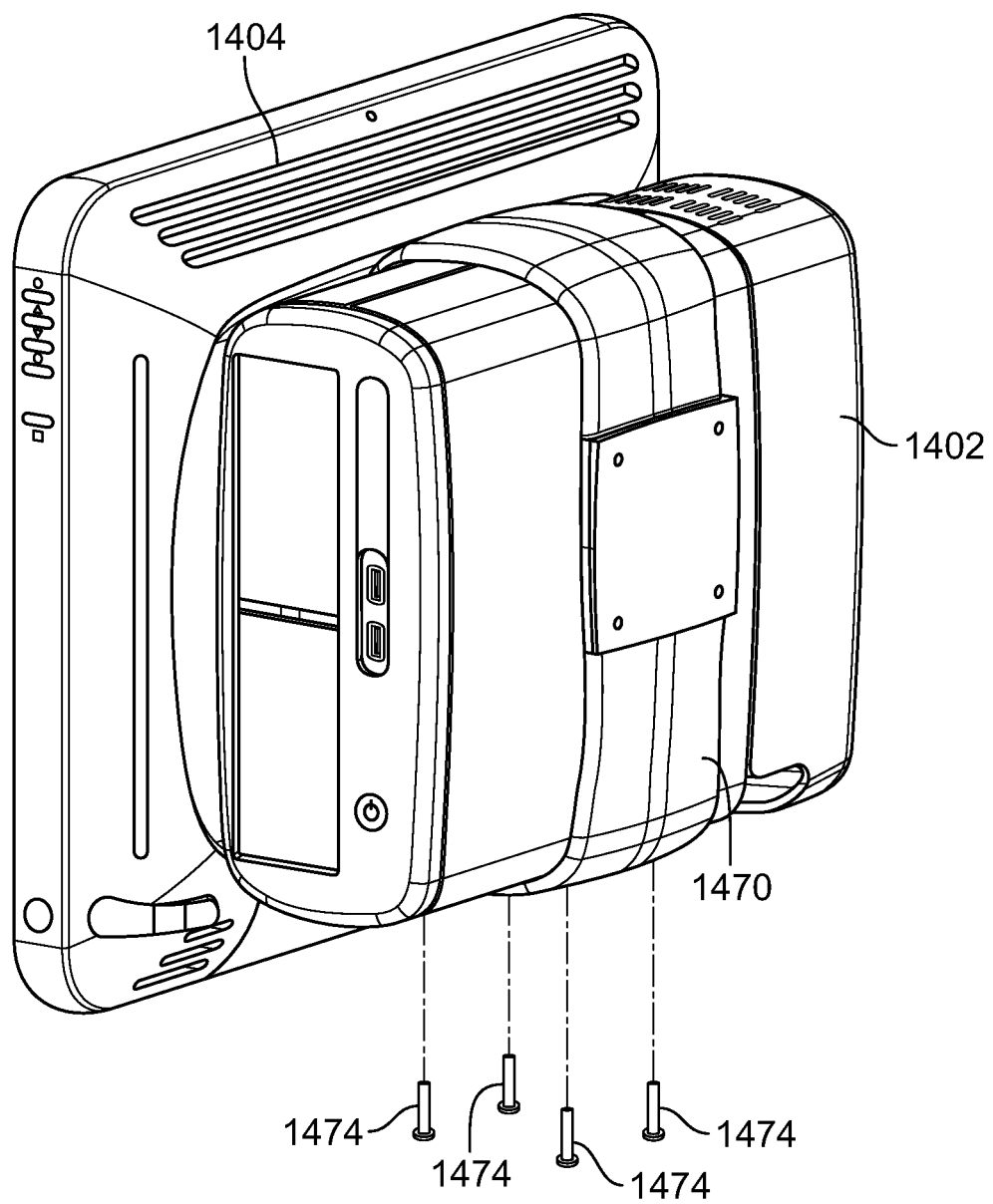
FIG. 14E is an oblique rear view illustration of one embodiment of a display with an attached bracket, depicting a monitor inserted into the bracket and being secured to said bracket for "backpack mounting"

FIG. 14e is an oblique rear view illustration of one embodiment of a display 1404 with an attached bracket 1470, depicting a monitor 1402 inserted into the bracket 1470 and being secured to said bracket 1470 for "backpack mounting". Four screws 1474 are inserted into the mounting holes (not shown) on the bottom of the bracket 1470 and are screwed into the monitor 1402 to secure the monitor 1402 to the bracket 1470 and enable "backpack mounting".

Figure 14F:
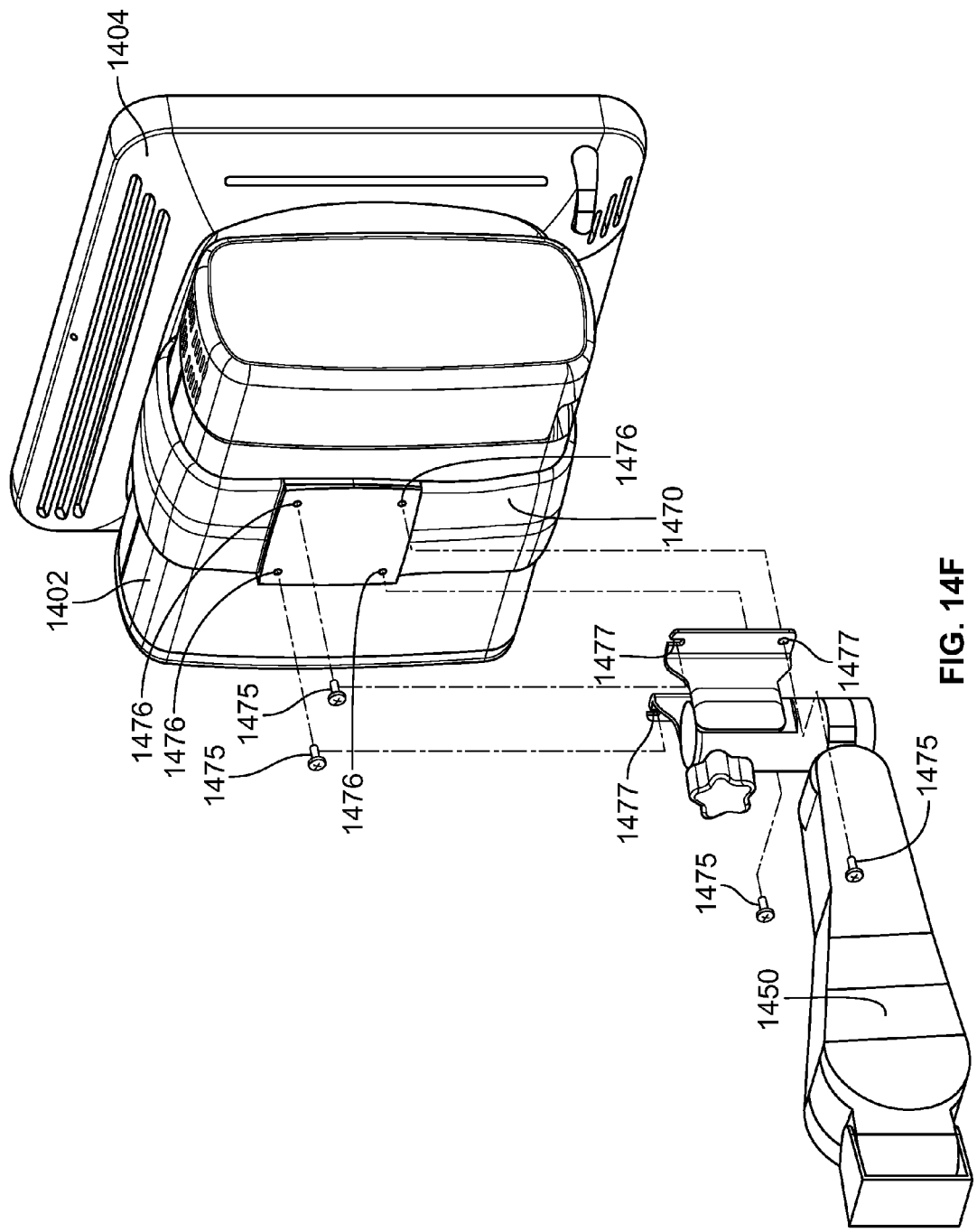
FIG. 14F is an oblique rear view illustration of one embodiment of a display and monitor connected together via a bracket, depicting the attachment of a support arm to said bracket.

FIG. 14f is an oblique rear view illustration of one embodiment of a display 1404 and monitor 1402 connected together via a bracket 1470, depicting the attachment of a support arm 1450 to said bracket 1470. Four screws 1475 are inserted into four holes or slots 1477 (only three are visible in FIG. 14f) on the end of the support arm 1450 and are screwed into the mounting holes 1476 in the bracket 1470. In one embodiment, the mounting holes or slots 1477 on the support arm 1450 and the holes in bracket 1470 are set in a standard 75 mm VESA pattern. In another embodiment, the mounting holes or slots 1477 on the support arm 1450 and the holes in bracket 1470 are set in a standard 100 mm VESA pattern.

Figure 15:
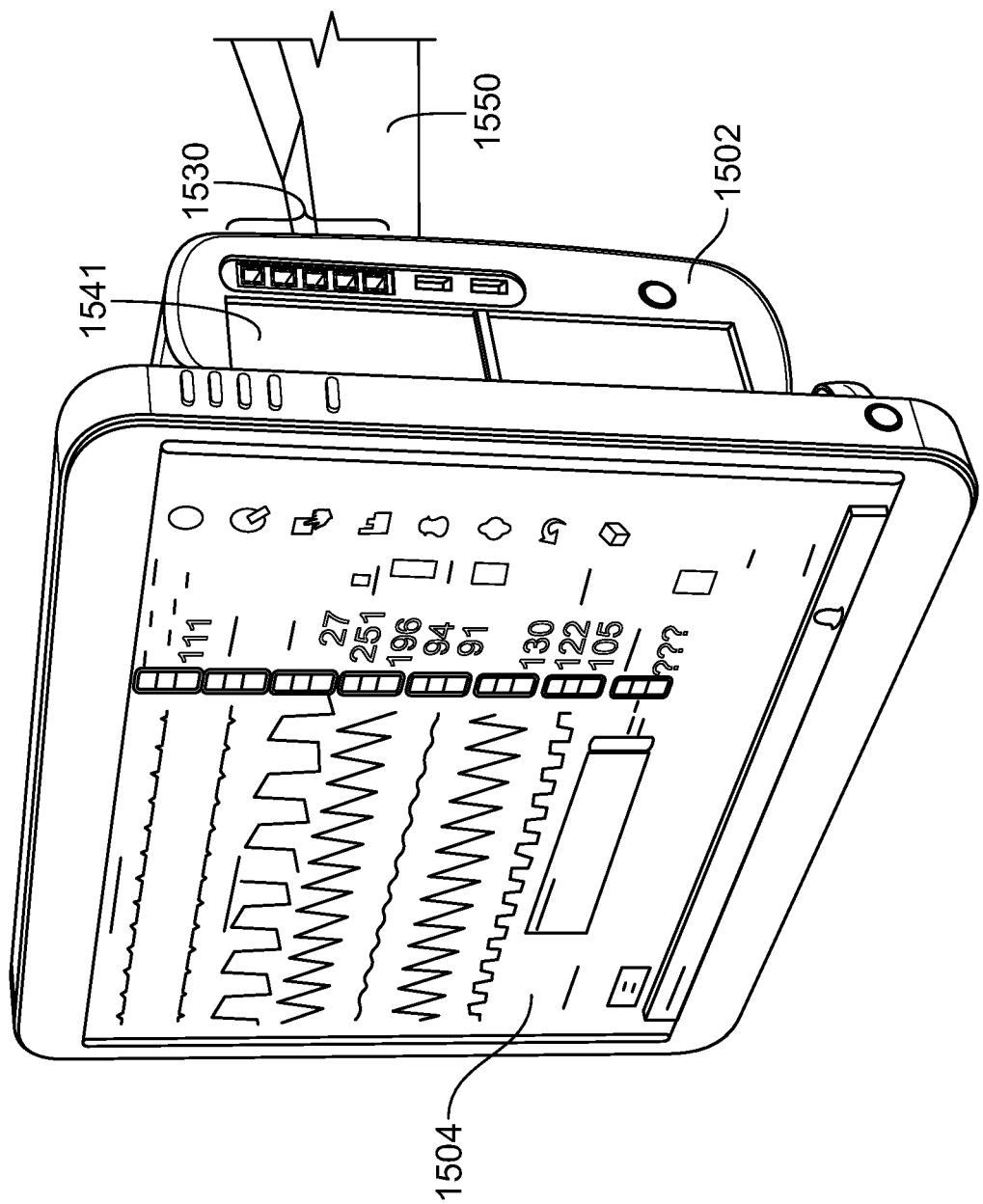
FIG. 15 is an oblique front view illustration of another embodiment of the monitor and external display connected together in the "backpack mounting" configuration and attached to a support arm.

FIG. 15 is an oblique front view illustration of another embodiment of the monitor 1502 and external display 1504 connected together in the "backpack mounting" configuration and attached to a support arm 1550. The back of the display 1504 is contoured to "nest" the monitor 1502 so that when attached together they appear to be one unit. This gives the system a cleaner look and also frees up valuable space around the patient bed. The "backpack mounting" feature enables reversible connection of the monitor 1502 to the display 1504. In this embodiment, the monitor 1502 is attached to the display 1504 so that the DSB connectors 1530 located on the front of the monitor 1502 are positioned toward the right side of the display 1504 when viewed from the front. This allows for the patient cables and USB devices that are attached to the system to extend from the right side. A door 1541 is in place over the module slot located on the front of the monitor 1504.

Figure 16:
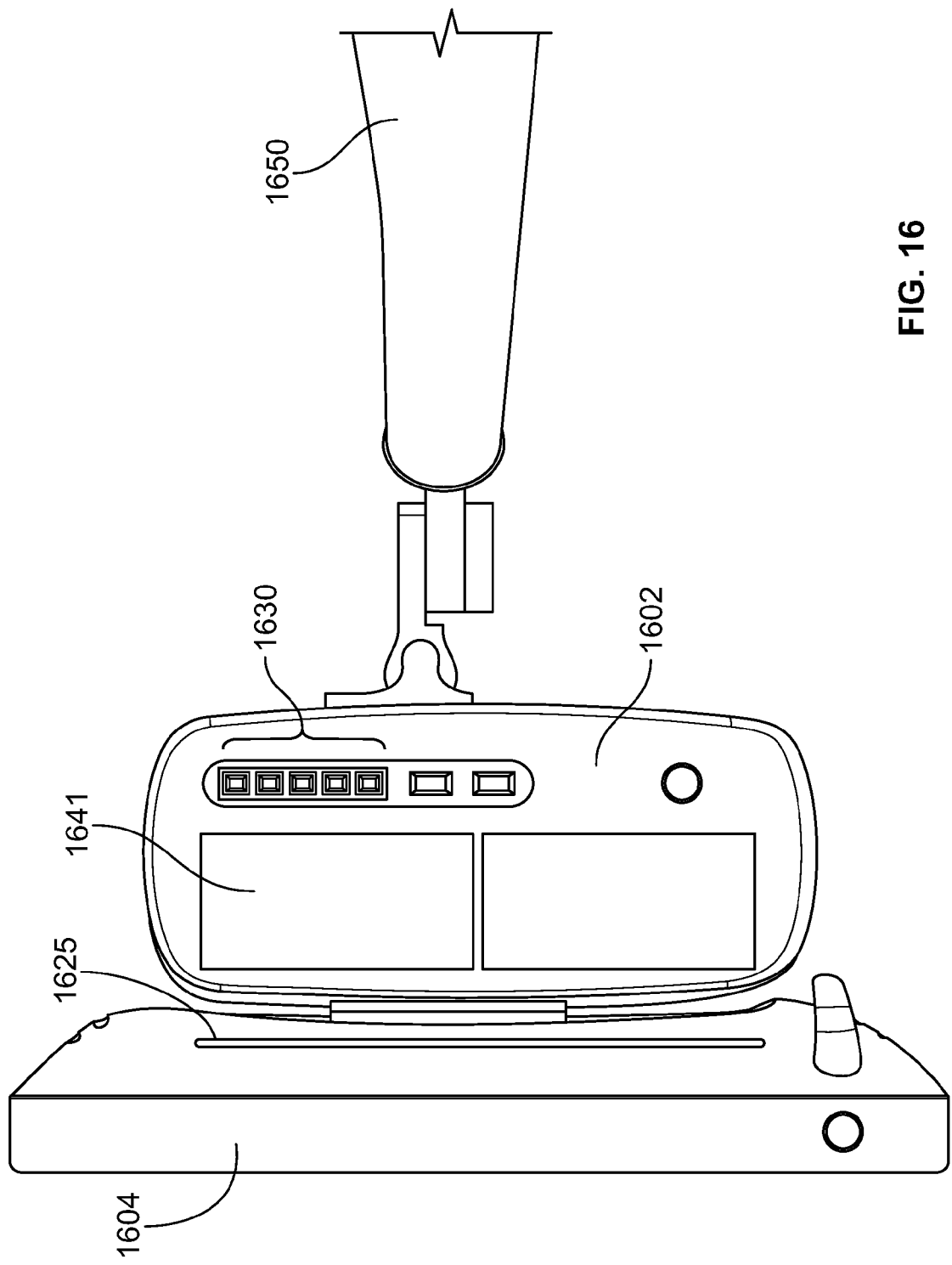
FIG. 16 is a side view illustration of the same embodiment of the monitor and external display connected together in the "backpack mounting" configuration and attached to a support arm as in FIG. 15.

FIG. 16 is a side view illustration of the same embodiment of the monitor 1602 and external display 1604 connected together in the "backpack mounting" configuration and attached to a support arm 1650 as in FIG. 15. The embodiment of FIG. 16 is viewed straight on from the right side. As in FIG. 15, patient cables and USB devices attached to the monitor 1602 would extend toward and then down from the right side of the display 1604 when viewed from the front. The DSB connectors 1630 and receptacle door/cover 1641 are visible in this figure. Also visible in this figure is the red alarm light 1625 located on the rear display enclosure.

Figure 17:
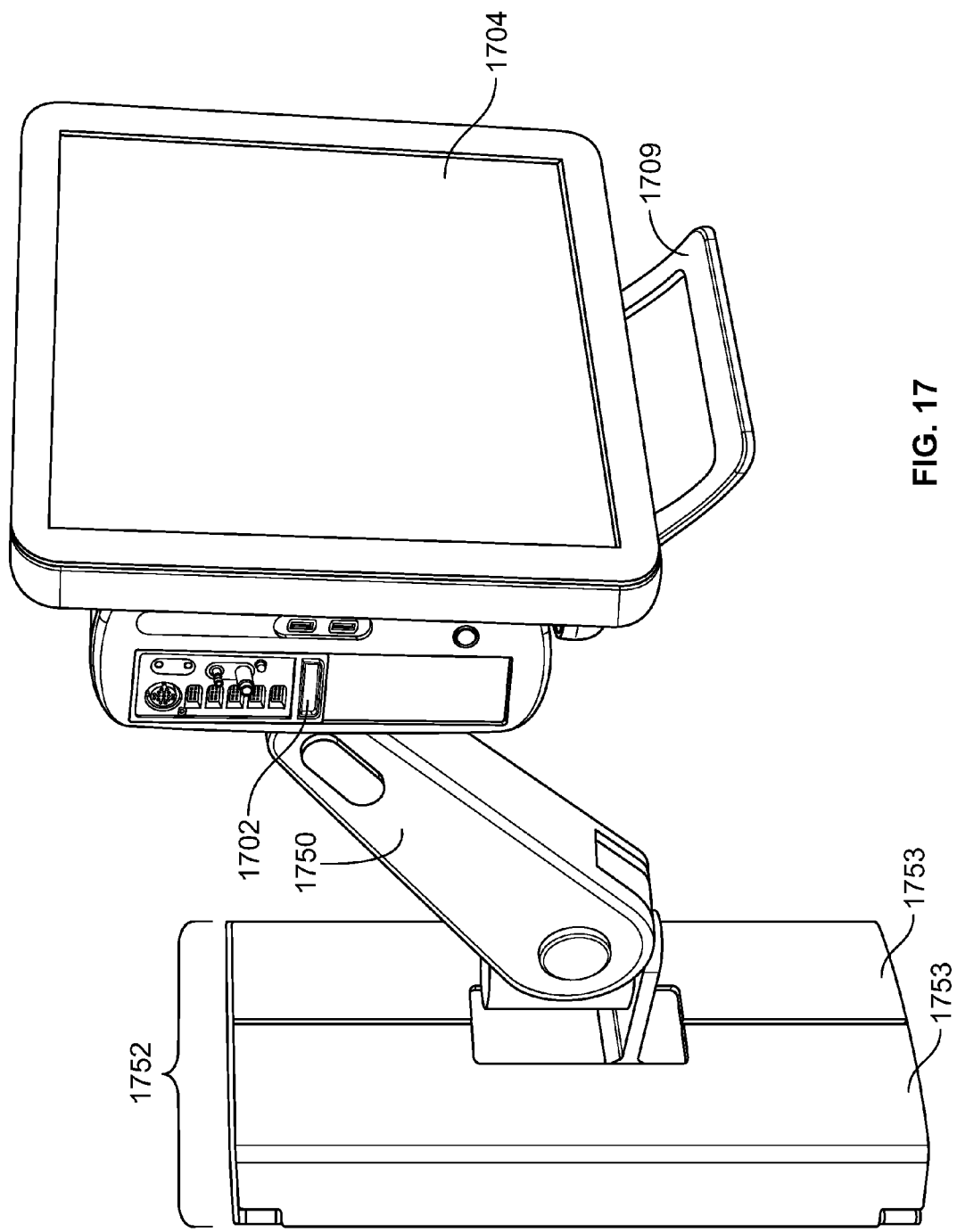
FIG. 17 is an oblique front view illustration of one embodiment of the monitor and external display connected together in the "backpack mounting" configuration and attached to a support arm, with an optional display cabinet attached to the wall track at the base of said arm.

FIG. 17 is an oblique front view illustration of one embodiment of the monitor 1702 and external display 1704 connected together in the "backpack mounting" configuration and attached to a support arm 1750, with an optional display cabinet 1752 attached to the wall track at the base of said arm 1750. In one embodiment, the display cabinet measures 11.3 inches wide×20.3 inches long×2.8 inches thick. In other embodiments, the display cabinet measures from 10.0 to 12.6 inches wide×18.3 to 22.3 inches long×2.4 to 3.2 inches thick. In one embodiment, when mounted to the wall or track, the display cabinet sits approximately 0.4 inches from said wall or track. In one embodiment, both doors of the display cabinet contain rectangular shaped cutouts located along the opening edge of said doors, midway between the top and bottom of said doors. When the doors are in the closed position, these cutouts form a rectangular shaped opening in the middle of the front of the display cabinet for passage of the support arm. In one embodiment, the opening measures 3.1 inches wide× 6.3 inches long. In other embodiments, the opening measures from 3.1 to 6.1 inches wide×6.3 to 10.3 inches long to accommodate larger support arms or additional support arms. In one embodiment, a similarly shaped cutout is included in the back of the display cabinet to accommodate the base of the support arm.

In the embodiment depicted in FIG. 17, the display 1704 also contains an optional handle 1709 and the monitor 1702 is attached to the display 1704 so that the receptacles are toward the left side of the display 1704 when viewed from the front. In one embodiment, the display cabinet 1752 houses the power supplies and dresses cables to give a cleaner appearance to the system. In one embodiment, the display cabinet 1752 can hold up to four power supplies. In one embodiment, the display cabinet 1752 contains mounting patterns to fix various items within the cabinet. In this figure, the doors 1753 of the display cabinet 1752 are closed. In one embodiment, the doors are held shut by magnets. In one embodiment, the display cabinet 1752 can be painted different colors to match the hospital environment. In one embodiment, the display cabinet 1752 contains removable plugs to allow cables to pass through. In one embodiment, the display cabinet 1752 contains brackets to attach cables to the outside of the cabinet.

Figure 18:
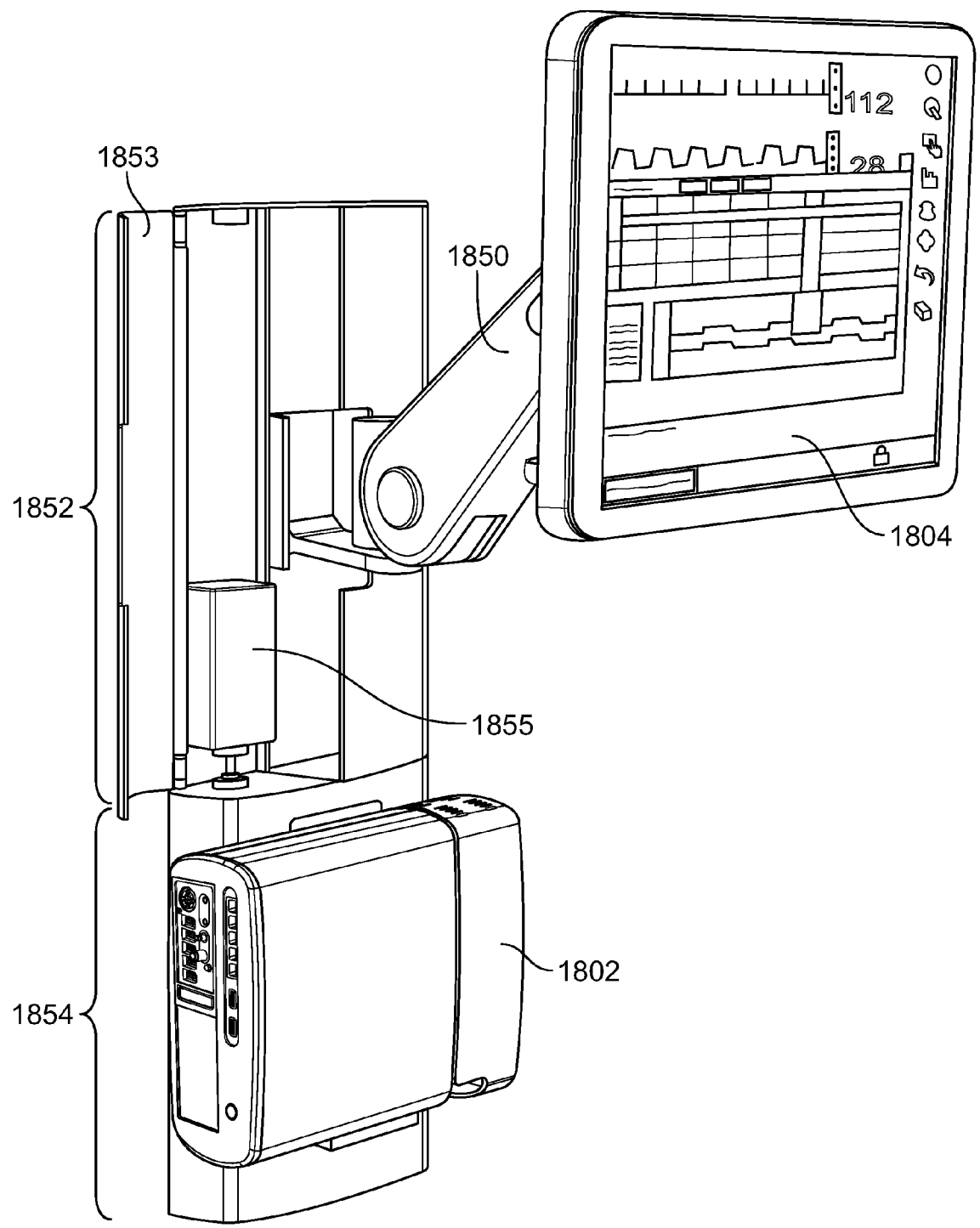
FIG. 18 is an oblique front view illustration of one embodiment of the external display attached to a support arm, with an optional display cabinet attached to the wall track at the base of said arm, and, an optional monitor cabinet, with attached monitor, installed onto the wall track below the display cabinet.

FIG. 18 is an oblique front view illustration of one embodiment of the external display 1804 attached to a support arm 1850, with an optional display cabinet 1852 attached to the wall track at the base of said arm 1850, and, an optional monitor cabinet 1854, with attached monitor 1802, installed onto the wall track below the display cabinet 1852. In one embodiment, the monitor cabinet measures 11.3 inches wide×16.1 inches long×2.8 inches thick. In other embodiments, the monitor cabinet measures from 10.0 to 12.6 inches wide×14.1 to 18.1 inches long×2.4 to 3.2 inches thick. In one embodiment, when mounted to the wall or track, the monitor cabinet sits approximately 0.4 inches from said wall or track. In one embodiment, the front surface of the monitor cabinet includes a large rectangular shaped cutout that is contoured to match the shape of the outside surface of the monitor. The contoured shape allows the monitor to "nest" snugly into monitor cabinet when mounted. In other embodiments, the shape of the cutout is square, oval, or any shape that matches the outside surface of the monitor.

The monitor cabinet 1854 supports reversible mounting of the monitor 1802. In this embodiment, the monitor 1802 is attached to the monitor cabinet 1854 so that the receptacles face toward the left of the wall track when viewed from the front. The monitor cabinet 1854 can also be mounted upside down. In one embodiment, the monitor cabinet 1854 is mounted on the wall track below the display cabinet. In another embodiment, the monitor cabinet 1854 is mounted on the wall track above the display cabinet. In another embodiment, the monitor cabinet 1854 is mounted on the wall track without the display cabinet. In one embodiment, the monitor cabinet 1854 stores the power supply for the monitor 1802. In one embodiment, the monitor cabinet 1854 contains removable plugs to allow for the passage of cables. Referring to FIG. 18, the left door 1853 of the display cabinet 1852 is open and the power supply 1855 for the display 1804 can be seen mounted within.

Figure 19:
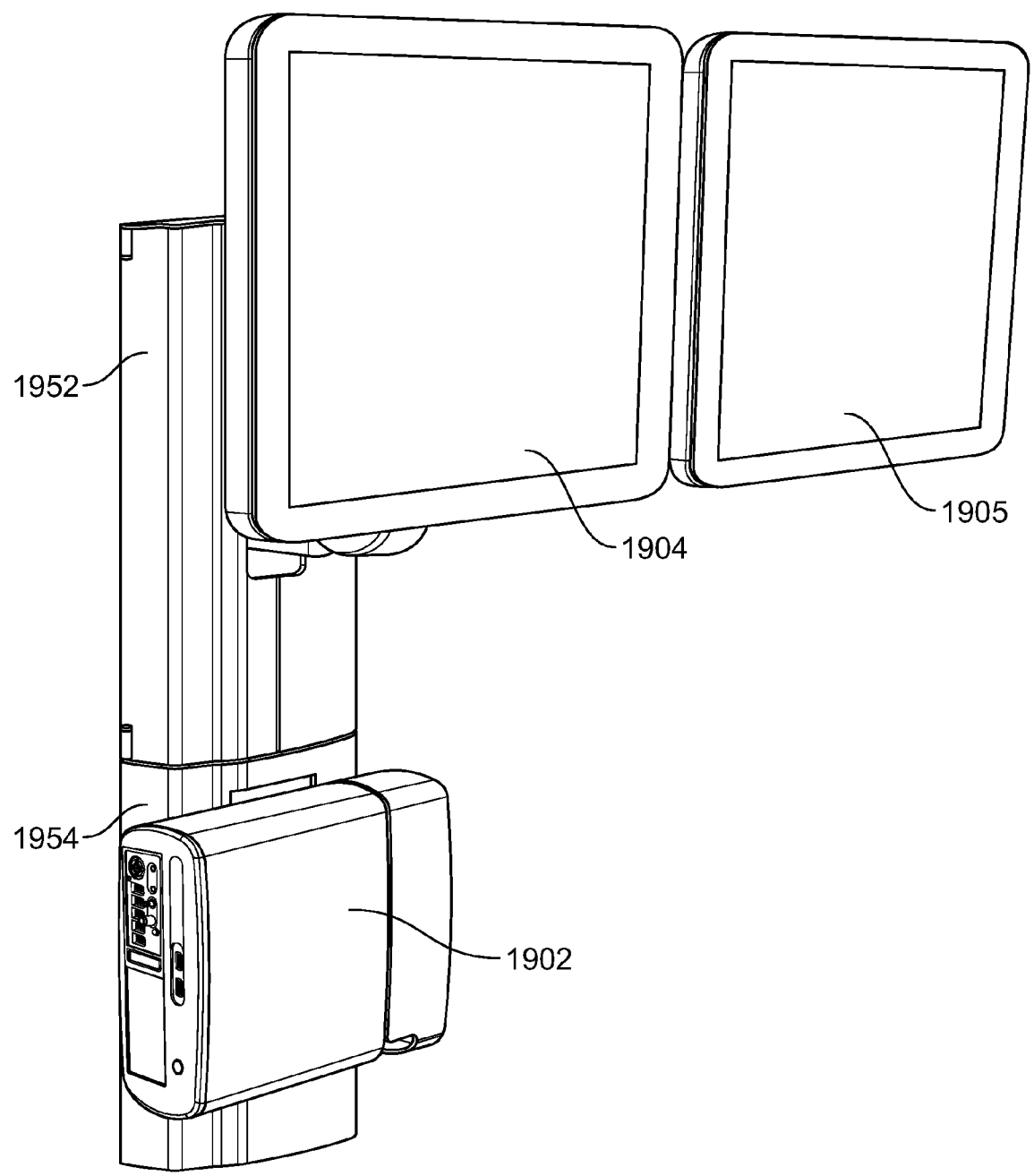
FIG. 19 is an oblique front view illustration of one embodiment of two external displays attached to support arms, with an optional display cabinet attached to the wall track at the base of said arms, and, an optional monitor cabinet, with attached monitor, installed onto the wall track below the display cabinet.

FIG. 19 is an oblique front view illustration of one embodiment of two external displays 1904, 1905 attached to support arms, with an optional display cabinet 1952 attached to the wall track at the base of said arms, and, an optional monitor cabinet 1954, with attached monitor 1902, installed onto the wall track below the display cabinet 1952. In this embodiment, the monitor 1902 is attached to the monitor cabinet 1954 so that the receptacles face toward the left side of the wall track when viewed from the front.

Figure 20:
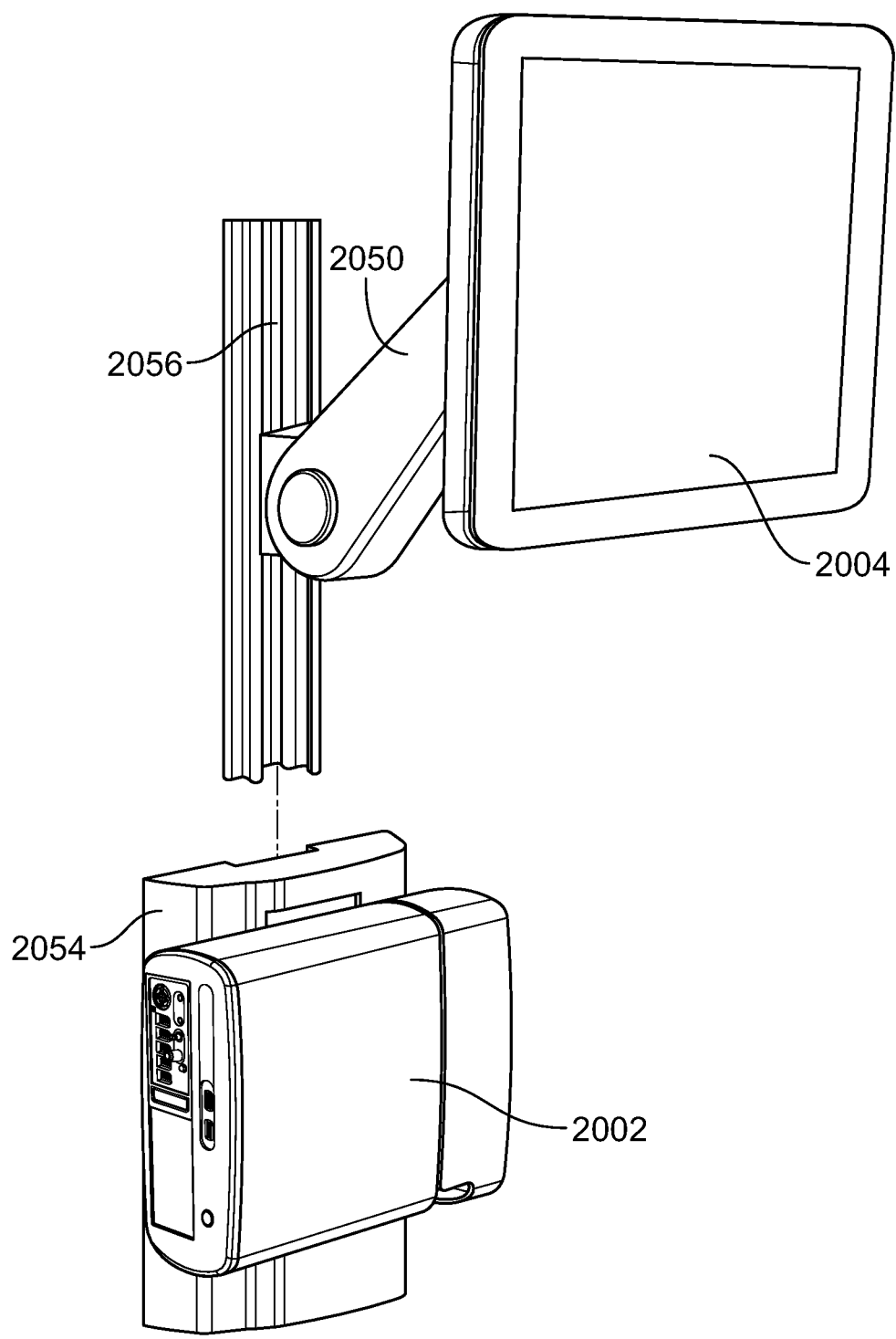
FIG. 20 is an oblique front view illustration of one embodiment of the external display attached to a support arm that is itself attached to a wall track, with an optional monitor cabinet, with attached monitor, installed onto the wall below said wall track; and, FIG. 21 is an oblique front view illustration of one embodiment of an exemplary command module of the patient monitoring system.

FIG. 20 is an oblique front view illustration of one embodiment of the external display 2004 attached to a support arm 2050 that is itself attached to a wall track 2056, with an optional monitor cabinet 2054, with attached monitor 2002, installed onto the wall below said wall track 2056. In this embodiment, the monitor 2002 is attached to the monitor cabinet 2054 so that the receptacles face toward the left side of the wall track 2056 when viewed from the front.

Figure 21:
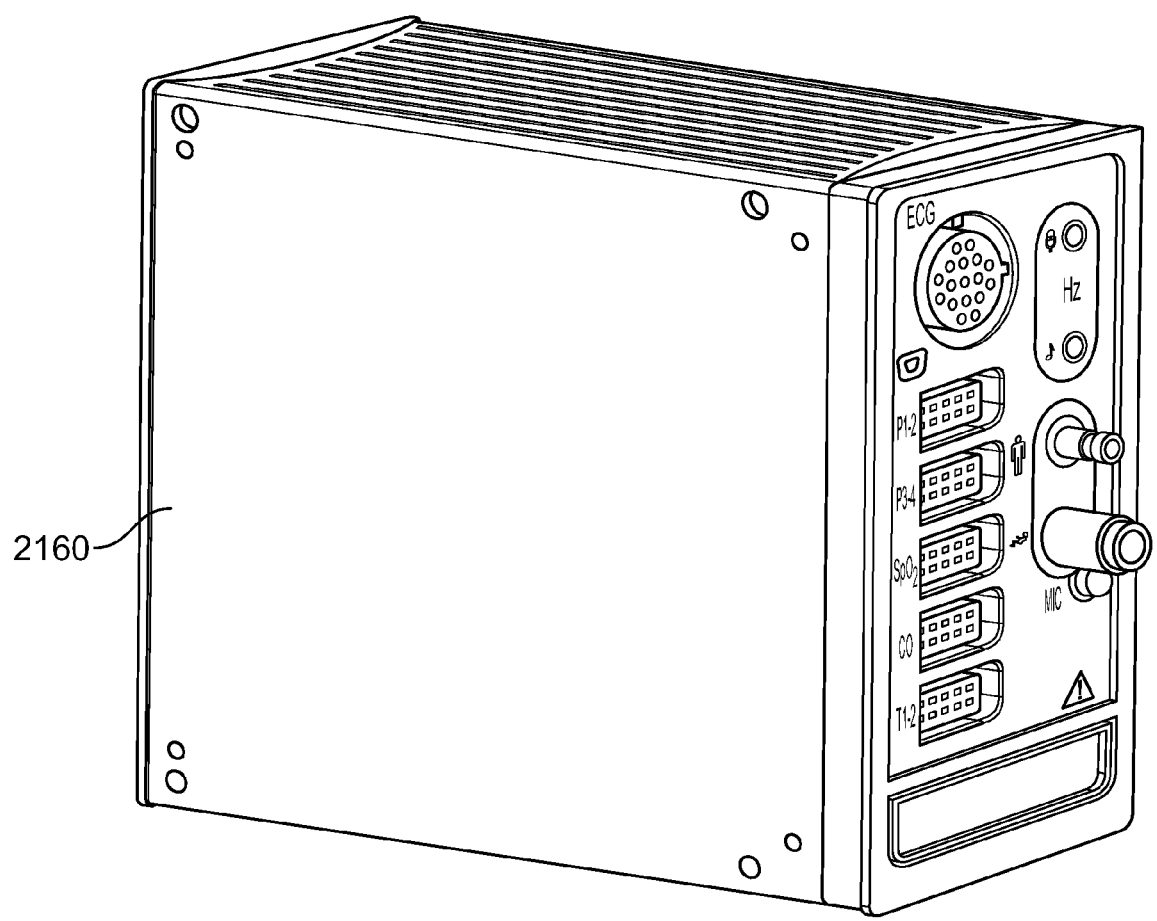

FIG. 21 is an oblique front view illustration of one embodiment of a command module 2160 of the patient monitoring system. In one embodiment, the command module can measure both adult and neonatal NIBP, IBP, ECG, SpO$_2$, cardiac output, and temperature and includes a stop button to manually override NIBP measurements. In one embodiment, the command module communicates via SDLC bus with and derives power from Spacelabs Healthcare monitors. In one embodiment, the command module contains internal memory to allow the module to be taken with a patient during transport and plugged into a separate monitor without losing data. In one embodiment, the module is enclosed by two pieces of sheet metal. In one embodiment, the module measures 2.2 inches wide by 4.5 inches high×7.0 inches thick. In other embodiments, the module measures from 1.9 to 2.5 inches wide×3.5 to 5.5 inches high×5.0 to 9.0 inches thick.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A patient monitoring system comprising:
a display device comprising:
a housing having a front side with a front face and a back side, said front side in combination with said back side defining an enclosure, wherein said enclosure comprises a first opening on a right side of the back side of said housing and a second opening on a left side of the back side of said housing;
a touchscreen mounted to the front face of said housing, wherein said touchscreen comprises a flat piece of glass having a central display area and a black border that extends along a left, right, top, and bottom edge of said glass;
a processor for determining an alarm state;
light sources within said touchscreen which are activated by said processor during the alarm state, wherein said light sources are configured to pass through said black border and concurrently pass through said first opening and second opening to provide a visual indicator of said alarm state to a user viewing said back side of the housing; and
a monitor for measuring a plurality of vital signs, wherein said monitor is in data communication with said display; and
a bracket for mounting the monitor behind the display device, the bracket comprising walls forming a hollow frame, wherein the hollow frame has a first side adapted to be mounted to a curved surface of the back side of the housing and wherein the monitor is mounted to the display device by insertion into the hollow frame.

2. The patient monitoring system of claim 1, further comprising a programmable capacitive button along the border of said touchscreen.

3. The patient monitoring system of claim 2, wherein said button comprises a metal capacitive piece.

4. The patient monitoring system of claim 1, further comprising a section of the touchscreen programmed for control of the alarm light.

5. The patient monitoring system of claim 1, wherein said black border is silk-screened on the back of the glass.

6. The patient monitoring system of claim 1, wherein said black border is comprised of an ink that is silk-screened or sprayed onto a masked out border area on the back of the glass.

7. The patient monitoring system of claim 1, wherein said black border contains small apertures that make the border appear continuous and uniform but allow light to pass through.

8. The patient monitoring system of claim 6, wherein the light sources which emit light passing through the black border are the same light sources which emit light passing through the first opening and second opening.

9. The patient monitoring system of claim 6, wherein the light sources which emit light passing through the black border are different than the light sources which emit light passing through the first opening and second opening.

10. A system for patient monitoring comprising:
a patient monitor that allows for communication with external devices, wherein said patient monitor is in electronic communication with and drives a display, and wherein said display comprises: a housing having a front side with a front face and a back side, said front side in combination with said back side defining an enclosure, wherein said enclosure comprises a first opening on a right side of the back side of said housing and a second opening on a left side of the back side of said housing; a touchscreen mounted to the front of said housing, wherein said touchscreen comprises a flat piece of glass having a central display area and a black border that extends along a left, right, top, and bottom edge of said glass;
a module for providing measurements of a plurality of patient parameters, wherein said module is in electronic communication with said patient monitor and wherein said module comprises at least one interface for electronically communicating with at least one patient parameter measurement device;
a processor for determining an alarm state; and, light sources within said touchscreen which are activated by said processor during the alarm state, wherein said light sources are configured to pass through said black border and concurrently pass through said first opening and second opening to provide a visual indicator of said alarm state to a user viewing said back side of the housing;

at least one Dual Serial Bus (DSB) interface for enabling electronic communication between the patient monitor, module, and/or patient parameter measuring device; and a bracket for mounting the patient monitor behind the display device, the bracket comprising walls forming a hollow frame, wherein the hollow frame has a first side adapted to be mounted to a curved surface of the back side of the display housing and wherein the monitor is mounted to the display by insertion into the hollow frame.

11. The system for patient monitoring of claim 10, wherein said display further comprises a single prominent, programmable capacitive button along the border of said touchscreen.

12. The system for patient monitoring of claim 11, wherein said button comprises a metal capacitive piece.

13. The system for patient monitoring of claim 10, wherein said display further comprises a section of the touchscreen programmed for control of the alarm light.

14. The system for patient monitoring of claim 10, wherein said black border is silk-screened on the back of the glass.

15. The system for patient monitoring of claim 10, wherein said black border is comprised of an ink that is silk-screened or sprayed onto a masked out border area on the back of the glass.

16. The system for patient monitoring of claim 10, wherein said black border contains small apertures that make the border appear continuous and uniform but allow light to pass through.

17. The system for patient monitoring of claim 10, wherein the light sources which emit light passing through the black border are the same light sources which emit light passing through the first opening and second opening.

18. The system for patient monitoring of claim 10, wherein the light sources which emit light passing through the black border are different than the light sources which emit light passing through the first opening and second opening.

19. The system for patient monitoring of claim 10, further comprising a display mounting cabinet.

20. The system for patient monitoring of claim 10, further comprising a monitor mounting cabinet.

* * * * *